United States Patent [19]
Montminy

[11] Patent Number: 5,750,336
[45] Date of Patent: May 12, 1998

[54] ASSAYS FOR THE IDENTIFICATION OF COMPOUNDS WHICH INHIBIT ACTIVATION OF CAMP AND MITOGEN RESPONSIVE GENES

[75] Inventor: Marc R. Montminy, Encinitas, Calif.

[73] Assignee: The Salk Institute for Biological Studies, La Jolla, Calif.

[21] Appl. No.: 194,468

[22] Filed: Feb. 10, 1994

[51] Int. Cl.$^6$ .......................... C12Q 1/68; G01N 33/567; C12N 15/85
[52] U.S. Cl. .............. 435/6; 435/7.21; 435/7.6; 435/7.8; 935/60; 935/110
[58] Field of Search ................ 435/6, 7.21, 7.6, 435/7.8, 7.92; 935/60, 110

[56] References Cited

U.S. PATENT DOCUMENTS 5,378,603  1/1995  Brown et al. ............................ 435/6
5,403,712  4/1995  Crabtree et al. ........................ 435/6

OTHER PUBLICATIONS

Lee et al., Transcriptional regulation by CREB abd its relatives, Biochim. Biophys. Acta 1174:221–233, 1993.
Masson et al., Identification of proteins that interact with CREB during differentiation of F9 embryonal carcinoma cells, Nucleic Acids Res. 21(5):1163–1169, 1993.
Alberts et al., "Protein Phosphatase 2A Potentiates Activity of Promoters Containing AP-1-Binding Elements", *Molecular an Cellular Biology* 13(4):2104–2112 (1993).
Brindle et al., "Protein-kinase-A-dependent activator in transcription factor CREB reveals new role for CREM repressors", *Nature* 364:821–824 (1993).
Boyle et al., "Activation of Protein Kinase C Decreases Phosphorylation of c–Jun at Sites That Negatively Regulate Its DNA–Binding Activity", *Cell* 64:573–584 (1991).
Chrivia et al., "Phosphorylated CREB binds specifically to the nuclear protein CBP", *Nature* 365:855–859 (1993).
Gonzalez, G.A., and Montminy, M.R., "Cyclic AMP Stimulates Somatostatin Gene Transcription by Phosphorylation of CREB at Serine 133", *Cell* 59:675–680 (1989).
Gonzalez et al., "Characterization of Motifs Which Are Critical for Activity of the Cyclic AMP–Responsive Transcription Factor CREB", *Molecular and Cellular Biology* 11(3):1306–1312 (1991).

Hagiwara et al., "Transcriptional Attenuation Following cAMP Induction Requires PP–1–Mediated Dephosphorylation of CREB", *Cell* 70:105–113 (1992).
Hibi et al., "Identification of an oncoprotein–and UV–responsive protein kinase that binds and potentiates the c–Jun activation domain", *Genes & Development* 7:2135–2148 (1993).
Hill et al., "Functional Analysis of a Growth Factor–Responsive Transcription Factor Complex", *Cell* 73:395–406 (1993).
Maguire et al., "HBV X Protein Alters the DNA binding Specificity of CREB and ATF–2 by Protein–Protein Interactions", *Science* 252:842–844 (1991).
Smeal et al., "Oncogenic and Transcriptional cooperation with Ha–Ras requires phosphorylation of c–Jun on serines 63 and 73", *Nature* 354:494–496 (1991).

Primary Examiner—Marian C. Knode
Assistant Examiner—Donna C. Wortman
Attorney, Agent, or Firm—Stephen E. Reiter; Gray Cary Ware & Freidenrich

[57] ABSTRACT

In accordance with the present invention, it has been discovered that CREB binding protein (CBP) cooperates with upstream activators involved in the activation of transcription of such signal dependent transcription factors as c–Jun (responsive to phorbol ester), serum response factor, and the like. It has also been discovered that CBP can be employed in an assay to identify compounds which disrupt the ability of such signal dependent transcription factors to activate transcription. In another aspect, it has been discovered that CBP can be employed in an assay to identify new signal dependent transcription factors. In yet another aspect of the present invention, it has been discovered that CBP can be employed in an assay to identify novel co-factor protein(s) which mediate the interaction between signal dependent transcription factors and inducer molecules involved in the activation of transcription. Accordingly, the present invention provides methods for the identification of compounds which inhibit activation of cAMP and mitogen responsive genes and methods for the identification of novel signal dependent transcription factors and co-factor proteins.

20 Claims, 2 Drawing Sheets

5,750,336

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 7326 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 1..7323

( x i ) SEQUENCE DESCRIPTION: SEQ ID NO:1:

```
ATG  GCC  GAG  AAC  TTG  CTG  GAC  GGA  CCG  CCC  AAC  CCC  AAA  CGA  GCC  AAA         48
Met  Ala  Glu  Asn  Leu  Leu  Asp  Gly  Pro  Pro  Asn  Pro  Lys  Arg  Ala  Lys
 1              5                        10                       15

CTC  AGC  TCG  CCC  GGC  TTC  TCC  GCG  AAT  GAC  AAC  ACA  GAT  TTT  GGA  TCA         96
Leu  Ser  Ser  Pro  Gly  Phe  Ser  Ala  Asn  Asp  Asn  Thr  Asp  Phe  Gly  Ser
                 20                       25                       30

TTG  TTT  GAC  TTG  GAA  AAT  GAC  CTT  CCT  GAT  GAG  CTG  ATC  CCC  AAT  GGA        144
Leu  Phe  Asp  Leu  Glu  Asn  Asp  Leu  Pro  Asp  Glu  Leu  Ile  Pro  Asn  Gly
         35                       40                       45

GAA  TTA  AGC  CTT  TTA  AAC  AGT  GGG  AAC  CTT  GTT  CCA  GAT  GCT  GCG  TCC        192
Glu  Leu  Ser  Leu  Leu  Asn  Ser  Gly  Asn  Leu  Val  Pro  Asp  Ala  Ala  Ser
     50                       55                       60

AAA  CAT  AAA  CAA  CTG  TCA  GAG  CTT  CTT  AGA  GGA  GGC  AGC  GGC  TCT  AGC        240
Lys  His  Lys  Gln  Leu  Ser  Glu  Leu  Leu  Arg  Gly  Gly  Ser  Gly  Ser  Ser
 65                       70                       75                       80

ATC  AAC  CCA  GGG  ATA  GGC  AAT  GTG  AGT  GCC  AGC  AGC  CCT  GTG  CAA  CAG        288
Ile  Asn  Pro  Gly  Ile  Gly  Asn  Val  Ser  Ala  Ser  Ser  Pro  Val  Gln  Gln
                          85                       90                       95

GGC  CTT  GGT  GGC  CAG  GCT  CAG  GGG  CAG  CCG  AAC  AGT  ACA  AAC  ATG  GCC        336
Gly  Leu  Gly  Gly  Gln  Ala  Gln  Gly  Gln  Pro  Asn  Ser  Thr  Asn  Met  Ala
                    100                      105                      110

AGC  TTA  GGT  GCC  ATG  GGC  AAG  AGC  CCT  CTG  AAC  CAA  GGA  GAC  TCA  TCA        384
Ser  Leu  Gly  Ala  Met  Gly  Lys  Ser  Pro  Leu  Asn  Gln  Gly  Asp  Ser  Ser
```

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  |  | 125 |  |  |  |  |
| ACA | CCC | AAC | CTG | CCC | AAA | CAG | GCA | GCC | AGC | ACC | TCT | GGG | CCC | ACT | CCC |
| Thr | Pro | Asn | Leu | Pro | Lys | Gln | Ala | Ala | Ser | Thr | Ser | Gly | Pro | Thr | Pro |
|  | 130 |  |  |  | 135 |  |  |  | 140 |  |  |  |  |  |  |
| CCT | GCC | TCC | CAA | GCA | CTG | AAT | CCA | CAA | GCA | CAA | AAG | CAA | GTA | GGG | CTG |
| Pro | Ala | Ser | Gln | Ala | Leu | Asn | Pro | Gln | Ala | Gln | Lys | Gln | Val | Gly | Leu |
| 145 |  |  |  |  | 150 |  |  |  |  | 155 |  |  |  |  | 160 |
| GTG | ACC | AGT | AGT | CCT | GCC | ACA | TCA | CAG | ACT | GGA | CCT | GGG | ATC | TGC | ATG |
| Val | Thr | Ser | Ser | Pro | Ala | Thr | Ser | Gln | Thr | Gly | Pro | Gly | Ile | Cys | Met |
|  |  |  |  | 165 |  |  |  |  | 170 |  |  |  |  | 175 |  |
| AAT | GCT | AAC | TTC | AAC | CAG | ACC | CAC | CCA | GGC | CTT | CTC | AAT | AGT | AAC | TCT |
| Asn | Ala | Asn | Phe | Asn | Gln | Thr | His | Pro | Gly | Leu | Leu | Asn | Ser | Asn | Ser |
|  |  |  | 180 |  |  |  |  | 185 |  |  |  |  | 190 |  |  |
| GGC | CAT | AGC | TTA | ATG | AAT | CAG | GCT | CAA | CAA | GGG | CAA | GCT | CAA | GTC | ATG |
| Gly | His | Ser | Leu | Met | Asn | Gln | Ala | Gln | Gln | Gly | Gln | Ala | Gln | Val | Met |
|  |  | 195 |  |  |  |  | 200 |  |  |  |  | 205 |  |  |  |
| AAT | GGA | TCT | CTT | GGG | GCT | GCT | GGA | AGA | GGA | AGG | GGA | GCT | GGA | ATG | CCC |
| Asn | Gly | Ser | Leu | Gly | Ala | Ala | Gly | Arg | Gly | Arg | Gly | Ala | Gly | Met | Pro |
|  | 210 |  |  |  |  | 215 |  |  |  |  | 220 |  |  |  |  |
| TAC | CCT | GCT | CCA | GCC | ATG | CAG | GGG | GCC | ACA | AGC | AGT | GTG | CTG | GCG | GAG |
| Tyr | Pro | Ala | Pro | Ala | Met | Gln | Gly | Ala | Thr | Ser | Ser | Val | Leu | Ala | Glu |
| 225 |  |  |  |  | 230 |  |  |  |  | 235 |  |  |  |  | 240 |
| ACC | TTG | ACA | CAG | GTT | TCC | CCA | CAA | ATG | GCT | GGC | CAT | GCT | GGA | CTA | AAT |
| Thr | Leu | Thr | Gln | Val | Ser | Pro | Gln | Met | Ala | Gly | His | Ala | Gly | Leu | Asn |
|  |  |  |  | 245 |  |  |  |  | 250 |  |  |  |  | 255 |  |
| ACA | GCA | CAG | GCA | GGA | GGC | ATG | ACC | AAG | ATG | GGA | ATG | ACT | GGT | ACC | ACA |
| Thr | Ala | Gln | Ala | Gly | Gly | Met | Thr | Lys | Met | Gly | Met | Thr | Gly | Thr | Thr |
|  |  |  | 260 |  |  |  |  | 265 |  |  |  |  | 270 |  |  |
| AGT | CCA | TTT | GGA | CAA | CCC | TTT | AGT | CAA | ACT | GGA | GGG | CAG | CAG | ATG | GGA |
| Ser | Pro | Phe | Gly | Gln | Pro | Phe | Ser | Gln | Thr | Gly | Gly | Gln | Gln | Met | Gly |
|  | 275 |  |  |  |  | 280 |  |  |  |  | 285 |  |  |  |  |
| GCC | ACT | GGA | GTG | AAC | CCC | CAG | TTA | GCC | AGC | AAA | CAG | AGC | ATG | GTC | AAT |
| Ala | Thr | Gly | Val | Asn | Pro | Gln | Leu | Ala | Ser | Lys | Gln | Ser | Met | Val | Asn |
|  | 290 |  |  |  |  | 295 |  |  |  |  | 300 |  |  |  |  |
| AGT | TTA | CCT | GCT | TTT | CCT | ACA | GAT | ATC | AAG | AAT | ACT | TCA | GTC | ACC | ACT |
| Ser | Leu | Pro | Ala | Phe | Pro | Thr | Asp | Ile | Lys | Asn | Thr | Ser | Val | Thr | Thr |
| 305 |  |  |  |  | 310 |  |  |  |  | 315 |  |  |  |  | 320 |
| GTG | CCA | AAT | ATG | TCC | CAG | TTG | CAA | ACA | TCA | GTG | GGA | ATT | GTA | CCC | ACA |
| Val | Pro | Asn | Met | Ser | Gln | Leu | Gln | Thr | Ser | Val | Gly | Ile | Val | Pro | Thr |
|  |  |  |  | 325 |  |  |  |  | 330 |  |  |  |  | 335 |  |
| CAA | GCA | ATT | GCA | ACA | GGC | CCC | ACA | GCA | GAC | CCT | GAA | AAA | CGC | AAA | CTG |
| Gln | Ala | Ile | Ala | Thr | Gly | Pro | Thr | Ala | Asp | Pro | Glu | Lys | Arg | Lys | Leu |
|  |  |  | 340 |  |  |  |  | 345 |  |  |  |  | 350 |  |  |
| ATA | CAG | CAG | CAG | CTG | GTT | CTA | CTG | CTT | CAT | GCC | CAC | AAA | TGT | CAG | AGA |
| Ile | Gln | Gln | Gln | Leu | Val | Leu | Leu | Leu | His | Ala | His | Lys | Cys | Gln | Arg |
|  |  | 355 |  |  |  |  | 360 |  |  |  |  | 365 |  |  |  |
| CGA | GAG | CAA | GCA | AAT | GGA | GAG | GTT | CGG | GCC | TGT | TCT | CTC | CCA | CAC | TGT |
| Arg | Glu | Gln | Ala | Asn | Gly | Glu | Val | Arg | Ala | Cys | Ser | Leu | Pro | His | Cys |
|  | 370 |  |  |  |  | 375 |  |  |  |  | 380 |  |  |  |  |
| CGA | ACC | ATG | AAA | AAC | GTT | TTG | AAT | CAC | ATG | ACA | CAT | TGT | CAG | GCT | CCC |
| Arg | Thr | Met | Lys | Asn | Val | Leu | Asn | His | Met | Thr | His | Cys | Gln | Ala | Pro |
| 385 |  |  |  |  | 390 |  |  |  |  | 395 |  |  |  |  | 400 |
| AAA | GCC | TGC | CAA | GTT | GCC | CAT | TGT | GCA | TCT | TCA | CGA | CAA | ATC | ATC | TCT |
| Lys | Ala | Cys | Gln | Val | Ala | His | Cys | Ala | Ser | Ser | Arg | Gln | Ile | Ile | Ser |
|  |  |  |  | 405 |  |  |  |  | 410 |  |  |  |  | 415 |  |
| CAT | TGG | AAG | AAC | TGC | ACA | CGA | CAT | GAC | TGT | CCT | GTT | TGC | CTC | CCT | TTG |
| His | Trp | Lys | Asn | Cys | Thr | Arg | His | Asp | Cys | Pro | Val | Cys | Leu | Pro | Leu |
|  |  |  | 420 |  |  |  |  | 425 |  |  |  |  | 430 |  |  |
| AAA | AAT | GCC | AGT | GAC | AAG | CGA | AAC | CAA | CAA | ACC | ATC | CTG | GGA | TCT | CCA |
| Lys | Asn | Ala | Ser | Asp | Lys | Arg | Asn | Gln | Gln | Thr | Ile | Leu | Gly | Ser | Pro |

432
480
528
576
624
672
720
768
816
864
912
960
1008
1056
1104
1152
1200
1248
1296
1344

```
                        435                           440                            445
GCT  AGT  GGA  ATT  CAA  AAC  ACA  ATT  GGT  TCT  GTT  GGT  GCA  GGG  CAA  CAG     1392
Ala  Ser  Gly  Ile  Gln  Asn  Thr  Ile  Gly  Ser  Val  Gly  Ala  Gly  Gln  Gln
     450                      455                           460

AAT  GCC  ACT  TCC  TTA  AGT  AAC  CCA  AAT  CCC  ATA  GAC  CCC  AGT  TCC  ATG     1440
Asn  Ala  Thr  Ser  Leu  Ser  Asn  Pro  Asn  Pro  Ile  Asp  Pro  Ser  Ser  Met
465                      470                           475                      480

CAG  CGG  GCC  TAT  GCT  GCT  CTA  GGA  CTC  CCC  TAC  ATG  AAC  CAG  CCT  CAG     1488
Gln  Arg  Ala  Tyr  Ala  Ala  Leu  Gly  Leu  Pro  Tyr  Met  Asn  Gln  Pro  Gln
                    485                           490                      495

ACG  CAG  CTG  CAG  CCT  CAG  GTT  CCT  GGC  CAG  CAA  CCA  GCA  CAG  CCT  CCA     1536
Thr  Gln  Leu  Gln  Pro  Gln  Val  Pro  Gly  Gln  Gln  Pro  Ala  Gln  Pro  Pro
               500                      505                           510

GCC  CAC  CAG  CAG  ATG  AGG  ACT  CTC  AAT  GCC  CTA  GGA  AAC  AAC  CCC  ATG     1584
Ala  His  Gln  Gln  Met  Arg  Thr  Leu  Asn  Ala  Leu  Gly  Asn  Asn  Pro  Met
          515                      520                           525

AGT  GTC  CCA  GCA  GGA  GGA  ATA  ACA  ACA  GAT  CAA  CAG  CCA  CCA  AAC  TTG     1632
Ser  Val  Pro  Ala  Gly  Gly  Ile  Thr  Thr  Asp  Gln  Gln  Pro  Pro  Asn  Leu
     530                      535                           540

ATT  TCA  GAA  TCA  GCT  CTT  CCA  ACT  TCC  TTG  GGG  GCT  ACC  AAT  CCA  CTG     1680
Ile  Ser  Glu  Ser  Ala  Leu  Pro  Thr  Ser  Leu  Gly  Ala  Thr  Asn  Pro  Leu
545                      550                           555                      560

ATG  AAT  GAT  GGT  TCA  AAC  TCT  GGT  AAC  ATT  GGA  AGC  CTC  AGC  ACG  ATA     1728
Met  Asn  Asp  Gly  Ser  Asn  Ser  Gly  Asn  Ile  Gly  Ser  Leu  Ser  Thr  Ile
                    565                           570                      575

CCT  ACA  GCA  GCG  CCT  CCT  TCC  AGC  ACT  GGT  GTT  CGA  AAA  GGC  TGG  CAT     1776
Pro  Thr  Ala  Ala  Pro  Pro  Ser  Ser  Thr  Gly  Val  Arg  Lys  Gly  Trp  His
               580                      585                           590

GAA  CAT  GTG  ACT  CAG  GAC  CTA  CGG  AGT  CAT  CTA  GTC  CAT  AAA  CTC  GTT     1824
Glu  His  Val  Thr  Gln  Asp  Leu  Arg  Ser  His  Leu  Val  His  Lys  Leu  Val
          595                      600                           605

CAA  GCC  ATC  TTC  CCA  ACT  CCA  GAC  CCT  GCA  GCT  CTG  AAA  GAT  CGC  CGC     1872
Gln  Ala  Ile  Phe  Pro  Thr  Pro  Asp  Pro  Ala  Ala  Leu  Lys  Asp  Arg  Arg
     610                      615                           620

ATG  GAG  AAC  CTG  GTT  GCC  TAT  GCT  AAG  AAA  GTG  GAG  GGA  GAC  ATG  TAT     1920
Met  Glu  Asn  Leu  Val  Ala  Tyr  Ala  Lys  Lys  Val  Glu  Gly  Asp  Met  Tyr
625                      630                           635                      640

GAG  TCT  GCT  AAT  AGC  AGG  GAT  GAA  TAC  TAT  CAT  TTA  TTA  GCA  GAG  AAA     1968
Glu  Ser  Ala  Asn  Ser  Arg  Asp  Glu  Tyr  Tyr  His  Leu  Leu  Ala  Glu  Lys
                    645                           650                      655

ATC  TAT  AAA  ATA  CAA  AAA  GAA  CTA  GAA  GAA  AAG  CGG  AGG  ACA  CGT  TTA     2016
Ile  Tyr  Lys  Ile  Gln  Lys  Glu  Leu  Glu  Glu  Lys  Arg  Arg  Thr  Arg  Leu
               660                      665                           670

CAT  AAG  CAA  GGC  ATC  CTG  GGT  AAC  CAG  CCA  GCT  TTA  CCA  GCT  TCT  GGG     2064
His  Lys  Gln  Gly  Ile  Leu  Gly  Asn  Gln  Pro  Ala  Leu  Pro  Ala  Ser  Gly
          675                      680                           685

GCT  CAG  CCC  CCT  GTG  ATT  CCA  CCA  GCC  CAG  TCT  GTA  AGA  CCT  CCA  AAT     2112
Ala  Gln  Pro  Pro  Val  Ile  Pro  Pro  Ala  Gln  Ser  Val  Arg  Pro  Pro  Asn
     690                      695                           700

GGG  CCC  CTG  CCT  TTG  CCA  GTG  AAT  CGC  ATG  CAG  GTT  TCT  CAA  GGG  ATG     2160
Gly  Pro  Leu  Pro  Leu  Pro  Val  Asn  Arg  Met  Gln  Val  Ser  Gln  Gly  Met
705                      710                           715                      720

AAT  TCA  TTT  AAC  CCA  ATG  TCC  CTG  GGA  AAC  GTC  CAG  TTG  CCA  CAG  GCA     2208
Asn  Ser  Phe  Asn  Pro  Met  Ser  Leu  Gly  Asn  Val  Gln  Leu  Pro  Gln  Ala
                    725                           730                      735

CCC  ATG  GGA  CCT  CGT  GCA  GCC  TCC  CCT  ATG  AAC  CAC  TCT  GTG  CAG  ATG     2256
Pro  Met  Gly  Pro  Arg  Ala  Ala  Ser  Pro  Met  Asn  His  Ser  Val  Gln  Met
               740                      745                           750

AAC  AGC  ATG  GCC  TCA  GTT  CCG  GGT  ATG  GCC  ATT  TCT  CCT  TCA  CGG  ATG     2304
Asn  Ser  Met  Ala  Ser  Val  Pro  Gly  Met  Ala  Ile  Ser  Pro  Ser  Arg  Met
```

|  |  |  |  |  |  |  |  |  |  |  |  |  |  |  |  |
|---|---|---|---|---|---|---|---|---|---|---|---|---|---|---|---|
|  | 755 |  |  |  |  | 760 |  |  |  |  | 765 |  |  |  |  |
| CCT | CAG | CCT | CCA | AAT | ATG | ATG | GGC | ACT | CAT | GCC | AAC | AAC | ATT | ATG | GCC |
| Pro | Gln | Pro | Pro | Asn | Met | Met | Gly | Thr | His | Ala | Asn | Asn | Ile | Met | Ala |
|  | 770 |  |  |  | 775 |  |  |  |  | 780 |  |  |  |  |  |
| CAG | GCA | CCT | ACT | CAG | AAC | CAG | TTT | CTG | CCA | CAG | AAC | CAG | TTT | CCA | TCA |
| Gln | Ala | Pro | Thr | Gln | Asn | Gln | Phe | Leu | Pro | Gln | Asn | Gln | Phe | Pro | Ser |
| 785 |  |  |  |  | 790 |  |  |  |  | 795 |  |  |  |  | 800 |
| TCC | AGT | GGG | GCA | ATG | AGT | GTG | AAC | AGT | GTG | GGC | ATG | GGG | CAA | CCA | GCA |
| Ser | Ser | Gly | Ala | Met | Ser | Val | Asn | Ser | Val | Gly | Met | Gly | Gln | Pro | Ala |
|  |  |  |  | 805 |  |  |  |  | 810 |  |  |  |  | 815 |  |
| GCC | CAG | GCA | GGT | GTT | TCA | CAG | GGT | CAG | GAA | CCT | GGA | GCT | GCT | CTC | CCT |
| Ala | Gln | Ala | Gly | Val | Ser | Gln | Gly | Gln | Glu | Pro | Gly | Ala | Ala | Leu | Pro |
|  |  |  | 820 |  |  |  |  | 825 |  |  |  |  | 830 |  |  |
| AAC | CCT | CTG | AAC | ATG | CTG | GCA | CCC | CAG | GCC | AGC | CAG | CTG | CCT | TGC | CCA |
| Asn | Pro | Leu | Asn | Met | Leu | Ala | Pro | Gln | Ala | Ser | Gln | Leu | Pro | Cys | Pro |
|  |  | 835 |  |  |  |  | 840 |  |  |  |  | 845 |  |  |  |
| CCA | GTG | ACA | CAG | TCA | CCA | TTG | CAC | CCG | ACT | CCA | CCT | CCT | GCT | TCC | ACA |
| Pro | Val | Thr | Gln | Ser | Pro | Leu | His | Pro | Thr | Pro | Pro | Pro | Ala | Ser | Thr |
|  |  | 850 |  |  |  |  | 855 |  |  |  |  | 860 |  |  |  |
| GCT | GCT | GGC | ATG | CCC | TCT | CTC | CAA | CAT | CCA | ACG | GCA | CCA | GGA | ATG | ACC |
| Ala | Ala | Gly | Met | Pro | Ser | Leu | Gln | His | Pro | Thr | Ala | Pro | Gly | Met | Thr |
| 865 |  |  |  |  | 870 |  |  |  |  | 875 |  |  |  |  | 880 |
| CCT | CCT | CAG | CCA | GCA | GCT | CCC | ACT | CAG | CCA | TCT | ACT | CCT | GTG | TCA | TCT |
| Pro | Pro | Gln | Pro | Ala | Ala | Pro | Thr | Gln | Pro | Ser | Thr | Pro | Val | Ser | Ser |
|  |  |  |  | 885 |  |  |  |  | 890 |  |  |  |  | 895 |  |
| GGG | CAG | ACT | CCT | ACC | CCA | ACT | CCT | GGC | TCA | GTG | CCC | AGC | GCT | GCC | CAA |
| Gly | Gln | Thr | Pro | Thr | Pro | Thr | Pro | Gly | Ser | Val | Pro | Ser | Ala | Ala | Gln |
|  |  |  | 900 |  |  |  |  | 905 |  |  |  |  | 910 |  |  |
| ACA | CAG | AGT | ACC | CCT | ACA | GTC | CAG | GCA | GCA | GCA | CAG | GCT | CAG | GTG | ACT |
| Thr | Gln | Ser | Thr | Pro | Thr | Val | Gln | Ala | Ala | Ala | Gln | Ala | Gln | Val | Thr |
|  |  | 915 |  |  |  |  | 920 |  |  |  |  | 925 |  |  |  |
| CCA | CAG | CCT | CAG | ACC | CCA | GTG | CAG | CCA | CCA | TCT | GTG | GCT | ACT | CCT | CAG |
| Pro | Gln | Pro | Gln | Thr | Pro | Val | Gln | Pro | Pro | Ser | Val | Ala | Thr | Pro | Gln |
|  | 930 |  |  |  |  | 935 |  |  |  |  | 940 |  |  |  |  |
| TCA | TCA | CAG | CAG | CAA | CCA | ACG | CCT | GTG | CAT | ACT | CAG | CCA | CCT | GGC | ACA |
| Ser | Ser | Gln | Gln | Gln | Pro | Thr | Pro | Val | His | Thr | Gln | Pro | Pro | Gly | Thr |
| 945 |  |  |  |  | 950 |  |  |  |  | 955 |  |  |  |  | 960 |
| CCG | CTT | TCT | CAG | GCA | GCA | GCC | AGC | ATT | GAT | AAT | AGA | GTC | CCT | ACT | CCC |
| Pro | Leu | Ser | Gln | Ala | Ala | Ala | Ser | Ile | Asp | Asn | Arg | Val | Pro | Thr | Pro |
|  |  |  |  | 965 |  |  |  |  | 970 |  |  |  |  | 975 |  |
| TCC | ACT | GTG | ACC | AGT | GCT | GAA | ACC | AGT | TCC | CAG | CAG | CCA | GGA | CCC | GAT |
| Ser | Thr | Val | Thr | Ser | Ala | Glu | Thr | Ser | Ser | Gln | Gln | Pro | Gly | Pro | Asp |
|  |  |  | 980 |  |  |  |  | 985 |  |  |  |  | 990 |  |  |
| GTG | CCC | ATG | CTG | GAA | ATG | AAG | ACA | GAG | GTG | CAG | ACA | GAT | GAT | GCT | GAG |
| Val | Pro | Met | Leu | Glu | Met | Lys | Thr | Glu | Val | Gln | Thr | Asp | Asp | Ala | Glu |
|  |  | 995 |  |  |  |  | 1000 |  |  |  |  | 1005 |  |  |  |
| CCT | GAA | CCT | ACT | GAA | TCC | AAG | GGG | GAA | CCT | CGG | TCT | GAG | ATG | ATG | GAA |
| Pro | Glu | Pro | Thr | Glu | Ser | Lys | Gly | Glu | Pro | Arg | Ser | Glu | Met | Met | Glu |
|  | 1010 |  |  |  |  | 1015 |  |  |  |  | 1020 |  |  |  |  |
| GAG | GAT | TTA | CAA | GGT | TCT | TCC | CAA | GTA | AAA | GAA | GAG | ACA | GAT | ACG | ACA |
| Glu | Asp | Leu | Gln | Gly | Ser | Ser | Gln | Val | Lys | Glu | Glu | Thr | Asp | Thr | Thr |
| 1025 |  |  |  |  | 1030 |  |  |  |  | 1035 |  |  |  |  | 1040 |
| GAG | CAG | AAG | TCA | GAG | CCA | ATG | GAA | GTA | GAA | GAA | AAG | AAA | CCT | GAA | GTA |
| Glu | Gln | Lys | Ser | Glu | Pro | Met | Glu | Val | Glu | Glu | Lys | Lys | Pro | Glu | Val |
|  |  |  |  | 1045 |  |  |  |  | 1050 |  |  |  |  | 1055 |  |
| AAA | GTG | GAA | GCT | AAA | GAG | GAA | GAA | GAG | AAC | AGT | TCG | AAC | GAC | ACA | GCC |
| Lys | Val | Glu | Ala | Lys | Glu | Glu | Glu | Glu | Asn | Ser | Ser | Asn | Asp | Thr | Ala |
|  |  |  | 1060 |  |  |  |  | 1065 |  |  |  |  | 1070 |  |  |
| TCA | CAA | TCA | ACA | TCT | CCT | TCC | CAG | CCA | CGC | AAA | AAA | ATC | TTT | AAA | CCC |
| Ser | Gln | Ser | Thr | Ser | Pro | Ser | Gln | Pro | Arg | Lys | Lys | Ile | Phe | Lys | Pro |

Line totals (right column): 2352, 2400, 2448, 2496, 2544, 2592, 2640, 2688, 2736, 2784, 2832, 2880, 2928, 2976, 3024, 3072, 3120, 3168, 3216, 3264

-continued

|  |  |  |  |
|---|---|---|---|
| GAG GAG CTA CGC CAG GCA CTT ATG CCA ACT CTA GAA GCA CTC TAT CGA<br>Glu Glu Leu Arg Gln Ala Leu Met Pro Thr Leu Glu Ala Leu Tyr Arg<br>　　1090　　　　　　　　1095　　　　　　　　　　1100 | 3312 |
| CAG GAC CCA GAG TCT TTG CCT TTT CGT CAG CCT GTA GAT CCT CAG CTC<br>Gln Asp Pro Glu Ser Leu Pro Phe Arg Gln Pro Val Asp Pro Gln Leu<br>1105　　　　　　　　1110　　　　　　　　1115　　　　　　　　　　1120 | 3360 |
| CTA GGA ATC CCA GAT TAT TTT GAT ATA GTG AAG AAT CCT ATG GAC CTT<br>Leu Gly Ile Pro Asp Tyr Phe Asp Ile Val Lys Asn Pro Met Asp Leu<br>　　　　　　　　1125　　　　　　　　1130　　　　　　　　　　1135 | 3408 |
| TCT ACC ATC AAA CGA AAG CTG GAC ACA GGG CAA TAT CAA GAA CCC TGG<br>Ser Thr Ile Lys Arg Lys Leu Asp Thr Gly Gln Tyr Gln Glu Pro Trp<br>　　　　1140　　　　　　　　1145　　　　　　　　　　1150 | 3456 |
| CAG TAT GTG GAT GAT GTC AGG CTT ATG TTC AAC AAT GCG TGG CTA TAT<br>Gln Tyr Val Asp Asp Val Arg Leu Met Phe Asn Asn Ala Trp Leu Tyr<br>1155　　　　　　　　1160　　　　　　　　　　1165 | 3504 |
| AAT CGT AAA ACG TCC CGT GTA TAT AAA TTT TGC AGT AAA CTT GCA GAG<br>Asn Arg Lys Thr Ser Arg Val Tyr Lys Phe Cys Ser Lys Leu Ala Glu<br>　　1170　　　　　　　　1175　　　　　　　　　　1180 | 3552 |
| GTC TTT GAA CAA GAA ATT GAC CCT GTC ATG CAG TCT CTT GGA TAT TGC<br>Val Phe Glu Gln Glu Ile Asp Pro Val Met Gln Ser Leu Gly Tyr Cys<br>1185　　　　　　　　1190　　　　　　　　1195　　　　　　　　　　1200 | 3600 |
| TGT GGA CGA AAG TAT GAG TTC TCC CCA CAG ACT TTG TGC TGT TAC GGA<br>Cys Gly Arg Lys Tyr Glu Phe Ser Pro Gln Thr Leu Cys Cys Tyr Gly<br>　　　　　　　　1205　　　　　　　　1210　　　　　　　　　　1215 | 3648 |
| AAG CAG CTG TGT ACA ATT CCT CGT GAT GCA GCC TAC TAC AGC TAT CAG<br>Lys Gln Leu Cys Thr Ile Pro Arg Asp Ala Ala Tyr Tyr Ser Tyr Gln<br>　　　　1220　　　　　　　　1225　　　　　　　　　　1230 | 3696 |
| AAT AGG TAT CAT TTC TGT GGG AAG TGT TTC ACA GAG ATC CAG GGC GAG<br>Asn Arg Tyr His Phe Cys Gly Lys Cys Phe Thr Glu Ile Gln Gly Glu<br>　　　　　　　　1235　　　　　　　　1240　　　　　　　　　　1245 | 3744 |
| AAT GTG ACC CTG GGT GAC GAC CCT TCC CAA CCT CAG ACG ACA ATT TCC<br>Asn Val Thr Leu Gly Asp Asp Pro Ser Gln Pro Gln Thr Thr Ile Ser<br>　　1250　　　　　　　　1255　　　　　　　　　　1260 | 3792 |
| AAG GAT CAA TTT GAA AAG AAG AAA AAT GAT ACC TTA GAT CCT GAA CCT<br>Lys Asp Gln Phe Glu Lys Lys Lys Asn Asp Thr Leu Asp Pro Glu Pro<br>1265　　　　　　　　1270　　　　　　　　1275　　　　　　　　　　1280 | 3840 |
| TTT GTT GAC TGC AAA GAG TGT GGC CGG AAG ATG CAT CAG ATT TGT GTT<br>Phe Val Asp Cys Lys Glu Cys Gly Arg Lys Met His Gln Ile Cys Val<br>　　　　　　　　1285　　　　　　　　1290　　　　　　　　　　1295 | 3888 |
| CTA CAC TAT GAC ATC ATT TGG CCT TCA GGT TTT GTG TGT GAC AAC TGT<br>Leu His Tyr Asp Ile Ile Trp Pro Ser Gly Phe Val Cys Asp Asn Cys<br>　　　　　　　　1300　　　　　　　　1305　　　　　　　　　　1310 | 3936 |
| TTG AAG AAA ACT GGC AGA CCT CGG AAA GAA AAC AAA TTC AGT GCT AAG<br>Leu Lys Lys Thr Gly Arg Pro Arg Lys Glu Asn Lys Phe Ser Ala Lys<br>　　　　1315　　　　　　　　1320　　　　　　　　　　1325 | 3984 |
| AGG CTG CAG ACC ACA CGA TTG GGA AAC CAC TTA GAA GAC AGA GTG AAT<br>Arg Leu Gln Thr Thr Arg Leu Gly Asn His Leu Glu Asp Arg Val Asn<br>　　　　1330　　　　　　　　1335　　　　　　　　　　1340 | 4032 |
| AAG TTT TTG CGG CGC CAG AAT CAC CCT GAA GCT GGG GAG GTT TTT GTC<br>Lys Phe Leu Arg Arg Gln Asn His Pro Glu Ala Gly Glu Val Phe Val<br>1345　　　　　　　　1350　　　　　　　　1355　　　　　　　　　　1360 | 4080 |
| AGA GTG GTG GCC AGC TCA GAC AAG ACT GTG GAG GTC AAG CCG GGA ATG<br>Arg Val Val Ala Ser Ser Asp Lys Thr Val Glu Val Lys Pro Gly Met<br>　　　　1365　　　　　　　　1370　　　　　　　　　　1375 | 4128 |
| AAG TCA AGG TTT GTG GAT TCT GGA GAG ATG TCG GAA TCT TTC CCA TAT<br>Lys Ser Arg Phe Val Asp Ser Gly Glu Met Ser Glu Ser Phe Pro Tyr<br>　　　　1380　　　　　　　　1385　　　　　　　　　　1390 | 4176 |
| CGT ACC AAA GCA CTC TTT GCT TTT GAG GAG ATC GAT GGA GTC GAT GTG<br>Arg Thr Lys Ala Leu Phe Ala Phe Glu Glu Ile Asp Gly Val Asp Val | 4224 |

```
                   1395                    1400                    1405

TGC TTT TTT GGG ATG CAT GTG CAA GAT ACG GCT CTG ATT GCC CCC CAC          4272
Cys Phe Phe Gly Met His Val Gln Asp Thr Ala Leu Ile Ala Pro His
    1410                1415                1420

CAA ATA CAA GGC TGT GTA TAC ATA TCT TAT CTG GAC AGT ATT CAT TTC          4320
Gln Ile Gln Gly Cys Val Tyr Ile Ser Tyr Leu Asp Ser Ile His Phe
1425                1430                1435                1440

TTC CGG CCC CGC TGC CTC CGG ACA GCT GTT TAC CAT GAG ATC CTC ATC          4368
Phe Arg Pro Arg Cys Leu Arg Thr Ala Val Tyr His Glu Ile Leu Ile
                1445                1450                1455

GGA TAT CTC GAG TAT GTG AAG AAA TTG GTG TAT GTG ACA GCA CAT ATT          4416
Gly Tyr Leu Glu Tyr Val Lys Lys Leu Val Tyr Val Thr Ala His Ile
            1460                1465                1470

TGG GCC TGT CCC CCA AGT GAA GGA GAT GAC TAT ATC TTT CAT TGC CAC          4464
Trp Ala Cys Pro Pro Ser Glu Gly Asp Asp Tyr Ile Phe His Cys His
        1475                1480                1485

CCC CCT GAC CAG AAA ATC CCC AAA CCA AAA CGA CTA CAG GAG TGG TAC          4512
Pro Pro Asp Gln Lys Ile Pro Lys Pro Lys Arg Leu Gln Glu Trp Tyr
    1490                1495                1500

AAG AAG ATG CTG GAC AAG GCG TTT GCA GAG AGG ATC ATT AAC GAC TAT          4560
Lys Lys Met Leu Asp Lys Ala Phe Ala Glu Arg Ile Ile Asn Asp Tyr
1505                1510                1515                1520

AAG GAC ATC TTC AAA CAA GCG AAC GAA GAC AGG CTC ACG AGT GCC AAG          4608
Lys Asp Ile Phe Lys Gln Ala Asn Glu Asp Arg Leu Thr Ser Ala Lys
                1525                1530                1535

GAG TTG CCC TAT TTT GAA GGA GAT TTC TGG CCT AAT GTG TTG GAA GAA          4656
Glu Leu Pro Tyr Phe Glu Gly Asp Phe Trp Pro Asn Val Leu Glu Glu
            1540                1545                1550

AGC ATT AAG GAA CTA GAA CAA GAA GAA GAA GAA AGG AAA AAA GAA GAG          4704
Ser Ile Lys Glu Leu Glu Gln Glu Glu Glu Glu Arg Lys Lys Glu Glu
        1555                1560                1565

AGT ACT GCA GCG AGT GAG ACT CCT GAG GGC AGT CAG GGT GAC AGC AAA          4752
Ser Thr Ala Ala Ser Glu Thr Pro Glu Gly Ser Gln Gly Asp Ser Lys
    1570                1575                1580

AAT GCG AAG AAA AAG AAC AAC AAG AAG ACC AAC AAA AAC AAA AGC AGC          4800
Asn Ala Lys Lys Lys Asn Asn Lys Lys Thr Asn Lys Asn Lys Ser Ser
1585                1590                1595                1600

ATT AGC CGC GCC AAC AAG AAG AAG CCC AGC ATG CCC AAT GTT TCC AAC          4848
Ile Ser Arg Ala Asn Lys Lys Lys Pro Ser Met Pro Asn Val Ser Asn
                1605                1610                1615

GAC CTG TCG CAG AAG CTG TAT GCC ACC ATG GAG AAG CAC AAG GAG GTA          4896
Asp Leu Ser Gln Lys Leu Tyr Ala Thr Met Glu Lys His Lys Glu Val
            1620                1625                1630

TTC TTT GTG ATT CAT CTG CAT GCT GGG CCT GTT ATC AGC ACT CAG CCC          4944
Phe Phe Val Ile His Leu His Ala Gly Pro Val Ile Ser Thr Gln Pro
        1635                1640                1645

CCC ATC GTG GAC CCT GAT CCT CTG CTT AGC TGT GAC CTC ATG GAT GGG          4992
Pro Ile Val Asp Pro Asp Pro Leu Leu Ser Cys Asp Leu Met Asp Gly
    1650                1655                1660

CGA GAT GCC TTC CTC ACC CTG GCC AGA GAC AAG CAC TGG GAA TTC TCT          5040
Arg Asp Ala Phe Leu Thr Leu Ala Arg Asp Lys His Trp Glu Phe Ser
1665                1670                1675                1680

TCC TTA CGC CGC TCC AAA TGG TCC ACT CTG TGC ATG CTG GTG GAG CTG          5088
Ser Leu Arg Arg Ser Lys Trp Ser Thr Leu Cys Met Leu Val Glu Leu
                1685                1690                1695

CAC ACA CAG GGC CAG GAC CGC TTT GTT TAT ACC TGC AAT GAG TGC AAA          5136
His Thr Gln Gly Gln Asp Arg Phe Val Tyr Thr Cys Asn Glu Cys Lys
            1700                1705                1710

CAC CAT GTG GAA ACA CGC TGG CAC TGC ACT GTG TGT GAG GAC TAT GAC          5184
His His Val Glu Thr Arg Trp His Cys Thr Val Cys Glu Asp Tyr Asp
```

```
                    1715                    1720                    1725
CTT TGT ATC AAT TGC TAC AAC ACA AAG AGC CAC ACC CAT AAG ATG GTG        5232
Leu Cys Ile Asn Cys Tyr Asn Thr Lys Ser His Thr His Lys Met Val
    1730                    1735                    1740

AAG TGG GGG CTA GGC CTA GAT GAT GAG GGC AGC AGT CAG GGT GAG CCA        5280
Lys Trp Gly Leu Gly Leu Asp Asp Glu Gly Ser Ser Gln Gly Glu Pro
1745                    1750                    1755                    1760

CAG TCC AAG AGC CCC CAG GAA TCC CGG CGT CTC AGC ATC CAG CGC TGC        5328
Gln Ser Lys Ser Pro Gln Glu Ser Arg Arg Leu Ser Ile Gln Arg Cys
                1765                    1770                    1775

ATC CAG TCC CTG GTG CAT GCC TGC CAG TGT CGC AAT GCC AAC TGC TCA        5376
Ile Gln Ser Leu Val His Ala Cys Gln Cys Arg Asn Ala Asn Cys Ser
            1780                    1785                    1790

CTG CCG TCT TGC CAG AAG ATG AAG CGA GTC GTG CAG CAC ACC AAG GGC        5424
Leu Pro Ser Cys Gln Lys Met Lys Arg Val Val Gln His Thr Lys Gly
        1795                    1800                    1805

TGC AAG CGC AAG ACT AAT GGA GGA TGC CCA GTG TGC AAG CAG CTC ATT        5472
Cys Lys Arg Lys Thr Asn Gly Gly Cys Pro Val Cys Lys Gln Leu Ile
    1810                    1815                    1820

GCT CTT TGC TGC TAC CAC GCC AAA CAC TGC CAA GAA AAT AAA TGC CCT        5520
Ala Leu Cys Cys Tyr His Ala Lys His Cys Gln Glu Asn Lys Cys Pro
1825                    1830                    1835                    1840

GTG CCC TTC TGC CTC AAC ATC AAA CAT AAC GTC CGC CAG CAG CAG ATC        5568
Val Pro Phe Cys Leu Asn Ile Lys His Asn Val Arg Gln Gln Gln Ile
                1845                    1850                    1855

CAG CAC TGC CTG CAG CAG GCT CAG CTC ATG CGC CGG CGA ATG GCA ACC        5616
Gln His Cys Leu Gln Gln Ala Gln Leu Met Arg Arg Arg Met Ala Thr
            1860                    1865                    1870

ATG AAC ACC CGC AAT GTG CCT CAG CAG AGT TTG CCT TCT CCT ACC TCA        5664
Met Asn Thr Arg Asn Val Pro Gln Gln Ser Leu Pro Ser Pro Thr Ser
        1875                    1880                    1885

GCA CCA CCC GGG ACT CCT ACA CAG CAG CCC AGC ACA CCC CAA ACA CCA        5712
Ala Pro Pro Gly Thr Pro Thr Gln Gln Pro Ser Thr Pro Gln Thr Pro
    1890                    1895                    1900

CAG CCC CCA GCC CAG CCT CAG CCT TCA CCT GTT AAC ATG TCA CCA GCA        5760
Gln Pro Pro Ala Gln Pro Gln Pro Ser Pro Val Asn Met Ser Pro Ala
1905                    1910                    1915                    1920

GGC TTC CCT AAT GTA GCC CGG ACT CAG CCC CCA ACA ATA GTG TCT GCT        5808
Gly Phe Pro Asn Val Ala Arg Thr Gln Pro Pro Thr Ile Val Ser Ala
                1925                    1930                    1935

GGG AAG CCT ACC AAC CAG GTG CCA GCT CCC CCA CCC CCT GCC CAG CCC        5856
Gly Lys Pro Thr Asn Gln Val Pro Ala Pro Pro Pro Ala Gln Pro
            1940                    1945                    1950

CCA CCT GCA GCA GTA GAA GCA GCC CGG CAA ATT GAA CGT GAG GCC CAG        5904
Pro Pro Ala Ala Val Glu Ala Ala Arg Gln Ile Glu Arg Glu Ala Gln
        1955                    1960                    1965

CAG CAG CAG CAC CTA TAC CGA GCA AAC ATC AAC AAT GGC ATG CCC CCA        5952
Gln Gln Gln His Leu Tyr Arg Ala Asn Ile Asn Asn Gly Met Pro Pro
    1970                    1975                    1980

GGA CGT GAC GGT ATG GGG ACC CCA GGA AGC CAA ATG ACT CCT GTG GGC        6000
Gly Arg Asp Gly Met Gly Thr Pro Gly Ser Gln Met Thr Pro Val Gly
1985                    1990                    1995                    2000

CTG AAT GTG CCC CGT CCC AAC CAA GTC AGT GGG CCT GTC ATG TCT AGT        6048
Leu Asn Val Pro Arg Pro Asn Gln Val Ser Gly Pro Val Met Ser Ser
                2005                    2010                    2015

ATG CCA CCT GGG CAG TGG CAG CAG GCA CCC ATC CCT CAG CAG CAG CCG        6096
Met Pro Pro Gly Gln Trp Gln Gln Ala Pro Ile Pro Gln Gln Gln Pro
            2020                    2025                    2030

ATG CCA GGC ATG CCC AGG CCT GTA ATG TCC ATG CAG GCC CAG GCA GCA        6144
Met Pro Gly Met Pro Arg Pro Val Met Ser Met Gln Ala Gln Ala Ala
```

-continued

```
              2035                    2040                    2045

GTG GCT GGG CCA CGG ATG CCC AAT GTG CAG CCA AAC AGG AGC ATC TCG      6192
Val Ala Gly Pro Arg Met Pro Asn Val Gln Pro Asn Arg Ser Ile Ser
2050                    2055                    2060

CCA AGT GCC CTG CAA GAC CTG CTA CGG ACC CTA AAG TCA CCC AGC TCT      6240
Pro Ser Ala Leu Gln Asp Leu Leu Arg Thr Leu Lys Ser Pro Ser Ser
2065                    2070                    2075                    2080

CCT CAG CAG CAG CAG CAG GTG CTG AAC ATC CTT AAA TCA AAC CCA CAG      6288
Pro Gln Gln Gln Gln Gln Val Leu Asn Ile Leu Lys Ser Asn Pro Gln
                    2085                    2090                    2095

CTA ATG GCA GCT TTC ATC AAA CAG CGC ACA GCC AAG TAT GTG GCC AAT      6336
Leu Met Ala Ala Phe Ile Lys Gln Arg Thr Ala Lys Tyr Val Ala Asn
                2100                    2105                    2110

CAG CCT GGC ATG CAG CCC CAG CCC GGA CTT CAA TCC CAG CCT GGT ATG      6384
Gln Pro Gly Met Gln Pro Gln Pro Gly Leu Gln Ser Gln Pro Gly Met
                2115                    2120                    2125

CAG CCC CAG CCT GGC ATG CAC CAG CAG CCT AGT TTG CAA AAC CTG AAC      6432
Gln Pro Gln Pro Gly Met His Gln Gln Pro Ser Leu Gln Asn Leu Asn
2130                    2135                    2140

GCA ATG CAA GCT GGT GTG CCA CGG CCT GGT GTG CCT CCA CCA CAA CCA      6480
Ala Met Gln Ala Gly Val Pro Arg Pro Gly Val Pro Pro Pro Gln Pro
2145                    2150                    2155                    2160

GCA ATG GGA GGC CTG AAT CCC CAG GGA CAA GCT CTG AAC ATC ATG AAC      6528
Ala Met Gly Gly Leu Asn Pro Gln Gly Gln Ala Leu Asn Ile Met Asn
                    2165                    2170                    2175

CCA GGA CAC AAC CCC AAC ATG ACA AAC ATG AAT CCA CAG TAC CGA GAA      6576
Pro Gly His Asn Pro Asn Met Thr Asn Met Asn Pro Gln Tyr Arg Glu
                2180                    2185                    2190

ATG GTG AGG AGA CAG CTG CTA CAG CAC CAG CAG CAG CAG CAG CAA CAG      6624
Met Val Arg Arg Gln Leu Leu Gln His Gln Gln Gln Gln Gln Gln Gln
                2195                    2200                    2205

CAG CAG CAG CAG CAG CAA CAA CAA AAT AGT GCC AGC TTG GCC GGG GGC      6672
Gln Gln Gln Gln Gln Gln Gln Gln Asn Ser Ala Ser Leu Ala Gly Gly
        2210                    2215                    2220

ATG GCG GGA CAC AGC CAG TTC CAG CAG CCA CAA GGA CCT GGA GGT TAT      6720
Met Ala Gly His Ser Gln Phe Gln Gln Pro Gln Gly Pro Gly Gly Tyr
2225                    2230                    2235                    2240

GCC CCA GCC ATG CAG CAG CAA CGC ATG CAA CAG CAC CTC CCC ATC CAG      6768
Ala Pro Ala Met Gln Gln Gln Arg Met Gln Gln His Leu Pro Ile Gln
                    2245                    2250                    2255

GGC AGC TCC ATG GGC CAG ATG GCT GCT CCA ATG GGA CAA CTT GGC CAG      6816
Gly Ser Ser Met Gly Gln Met Ala Ala Pro Met Gly Gln Leu Gly Gln
                2260                    2265                    2270

ATG GGG CAG CCT GGG CTA GGG GCA GAC AGC ACC CCT AAT ATC CAG CAG      6864
Met Gly Gln Pro Gly Leu Gly Ala Asp Ser Thr Pro Asn Ile Gln Gln
            2275                    2280                    2285

GCC CTG CAG CAA CGG ATT CTG CAG CAG CAG CAG ATG AAG CAA CAA ATT      6912
Ala Leu Gln Gln Arg Ile Leu Gln Gln Gln Gln Met Lys Gln Gln Ile
2290                    2295                    2300

GGG TCA CCA GGC CAG CCG AAC CCC ATG AGC CCC CAG CAG CAC ATG CTC      6960
Gly Ser Pro Gly Gln Pro Asn Pro Met Ser Pro Gln Gln His Met Leu
2305                    2310                    2315                    2320

TCA GGA CAG CCA CAG GCC TCA CAT CTC CCT GGC CAG CAG ATC GCC ACA      7008
Ser Gly Gln Pro Gln Ala Ser His Leu Pro Gly Gln Gln Ile Ala Thr
                    2325                    2330                    2335

TCC CTT AGT AAC CAG GTG CGA TCT CCA GCC CCT GTG CAG TCT CCA CGG      7056
Ser Leu Ser Asn Gln Val Arg Ser Pro Ala Pro Val Gln Ser Pro Arg
                2340                    2345                    2350

CCC CAA TCC CAA CCT CCA CAT TCC AGC CCG TCA CCA CGG ATA CAA CCC      7104
Pro Gln Ser Gln Pro Pro His Ser Ser Pro Ser Pro Arg Ile Gln Pro
```

| | | | | | | | | | | | | | | | |
|---|---|---|---|---|---|---|---|---|---|---|---|---|---|---|---|
| | | 2355 | | | | | 2360 | | | | | 2365 | | | |
| CAG | CCT | TCA | CCA | CAC | CAT | GTT | TCA | CCC | CAG | ACT | GGA | ACC | CCT | CAC | CCT | 7152 |
| Gln | Pro | Ser | Pro | His | His | Val | Ser | Pro | Gln | Thr | Gly | Thr | Pro | His | Pro | |
| 2370 | | | | | 2375 | | | | | 2380 | | | | | | |
| GGA | CTC | GCA | GTC | ACC | ATG | GCC | AGC | TCC | ATG | GAT | CAG | GGA | CAC | CTG | GGG | 7200 |
| Gly | Leu | Ala | Val | Thr | Met | Ala | Ser | Ser | Met | Asp | Gln | Gly | His | Leu | Gly | |
| 2385 | | | | | 2390 | | | | | 2395 | | | | | 2400 | |
| AAC | CCT | GAA | CAG | AGT | GCA | ATG | CTC | CCC | CAG | CTG | AAT | ACC | CCC | AAC | AGG | 7248 |
| Asn | Pro | Glu | Gln | Ser | Ala | Met | Leu | Pro | Gln | Leu | Asn | Thr | Pro | Asn | Arg | |
| | | | | 2405 | | | | | 2410 | | | | | 2415 | | |
| AGC | GCA | CTG | TCC | AGT | GAA | CTG | TCC | CTG | GTT | GGT | GAT | ACC | ACG | GGA | GAC | 7296 |
| Ser | Ala | Leu | Ser | Ser | Glu | Leu | Ser | Leu | Val | Gly | Asp | Thr | Thr | Gly | Asp | |
| | | | 2420 | | | | | 2425 | | | | | 2430 | | | |
| ACA | CTA | GAA | AAG | TTT | GTG | GAG | GGT | TTG | TAG | | | | | | | 7326 |
| Thr | Leu | Glu | Lys | Phe | Val | Glu | Gly | Leu | | | | | | | | |
| | | | 2435 | | | | | 2440 | | | | | | | | |

( 2 ) INFORMATION FOR SEQ ID NO:2:

( i ) SEQUENCE CHARACTERISTICS:
( A ) LENGTH: 2441 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Glu | Asn | Leu | Leu | Asp | Gly | Pro | Pro | Asn | Pro | Lys | Arg | Ala | Lys |
| 1 | | | | 5 | | | | | 10 | | | | | 15 | |
| Leu | Ser | Ser | Pro | Gly | Phe | Ser | Ala | Asn | Asp | Asn | Thr | Asp | Phe | Gly | Ser |
| | | | 20 | | | | | 25 | | | | | 30 | | |
| Leu | Phe | Asp | Leu | Glu | Asn | Asp | Leu | Pro | Asp | Glu | Leu | Ile | Pro | Asn | Gly |
| | | 35 | | | | | 40 | | | | | 45 | | | |
| Glu | Leu | Ser | Leu | Leu | Asn | Ser | Gly | Asn | Leu | Val | Pro | Asp | Ala | Ala | Ser |
| | 50 | | | | | 55 | | | | | 60 | | | | |
| Lys | His | Lys | Gln | Leu | Ser | Glu | Leu | Leu | Arg | Gly | Gly | Ser | Gly | Ser | Ser |
| 65 | | | | | 70 | | | | | 75 | | | | | 80 |
| Ile | Asn | Pro | Gly | Ile | Gly | Asn | Val | Ser | Ala | Ser | Ser | Pro | Val | Gln | Gln |
| | | | | 85 | | | | | 90 | | | | | 95 | |
| Gly | Leu | Gly | Gly | Gln | Ala | Gln | Gly | Gln | Pro | Asn | Ser | Thr | Asn | Met | Ala |
| | | | 100 | | | | | 105 | | | | | 110 | | |
| Ser | Leu | Gly | Ala | Met | Gly | Lys | Ser | Pro | Leu | Asn | Gln | Gly | Asp | Ser | Ser |
| | | 115 | | | | | 120 | | | | | 125 | | | |
| Thr | Pro | Asn | Leu | Pro | Lys | Gln | Ala | Ala | Ser | Thr | Ser | Gly | Pro | Thr | Pro |
| | 130 | | | | | 135 | | | | | 140 | | | | |
| Pro | Ala | Ser | Gln | Ala | Leu | Asn | Pro | Gln | Ala | Gln | Lys | Gln | Val | Gly | Leu |
| 145 | | | | | 150 | | | | | 155 | | | | | 160 |
| Val | Thr | Ser | Ser | Pro | Ala | Thr | Ser | Gln | Thr | Gly | Pro | Gly | Ile | Cys | Met |
| | | | | 165 | | | | | 170 | | | | | 175 | |
| Asn | Ala | Asn | Phe | Asn | Gln | Thr | His | Pro | Gly | Leu | Leu | Asn | Ser | Asn | Ser |
| | | | 180 | | | | | 185 | | | | | 190 | | |
| Gly | His | Ser | Leu | Met | Asn | Gln | Ala | Gln | Gln | Gly | Gln | Ala | Gln | Val | Met |
| | | 195 | | | | | 200 | | | | | 205 | | | |
| Asn | Gly | Ser | Leu | Gly | Ala | Ala | Gly | Arg | Gly | Arg | Gly | Ala | Gly | Met | Pro |
| | 210 | | | | | 215 | | | | | 220 | | | | |
| Tyr | Pro | Ala | Pro | Ala | Met | Gln | Gly | Ala | Thr | Ser | Ser | Val | Leu | Ala | Glu |
| 225 | | | | | 230 | | | | | 235 | | | | | 240 |
| Thr | Leu | Thr | Gln | Val | Ser | Pro | Gln | Met | Ala | Gly | His | Ala | Gly | Leu | Asn |

|     |     |     |     |     | 245 |     |     |     |     | 250 |     |     |     |     | 255 |     |
| --- | --- | --- | --- | --- | --- | --- | --- | --- | --- | --- | --- | --- | --- | --- | --- | --- |
| Thr | Ala | Gln | Ala<br>260 | Gly | Gly | Met | Thr | Lys<br>265 | Met | Gly | Met | Thr | Gly<br>270 | Thr | Thr |
| Ser | Pro | Phe<br>275 | Gly | Gln | Pro | Phe | Ser<br>280 | Gln | Thr | Gly | Gly | Gln<br>285 | Gln | Met | Gly |
| Ala | Thr<br>290 | Gly | Val | Asn | Pro | Gln<br>295 | Leu | Ala | Ser | Lys | Gln<br>300 | Ser | Met | Val | Asn |
| Ser<br>305 | Leu | Pro | Ala | Phe | Pro<br>310 | Thr | Asp | Ile | Lys | Asn<br>315 | Thr | Ser | Val | Thr | Thr<br>320 |
| Val | Pro | Asn | Met | Ser<br>325 | Gln | Leu | Gln | Thr | Ser<br>330 | Val | Gly | Ile | Val | Pro<br>335 | Thr |
| Gln | Ala | Ile | Ala<br>340 | Thr | Gly | Pro | Thr | Ala<br>345 | Asp | Pro | Glu | Lys | Arg<br>350 | Lys | Leu |
| Ile | Gln | Gln<br>355 | Gln | Leu | Val | Leu | Leu<br>360 | Leu | His | Ala | His | Lys<br>365 | Cys | Gln | Arg |
| Arg | Glu<br>370 | Gln | Ala | Asn | Gly | Glu<br>375 | Val | Arg | Ala | Cys | Ser<br>380 | Leu | Pro | His | Cys |
| Arg<br>385 | Thr | Met | Lys | Asn | Val<br>390 | Leu | Asn | His | Met | Thr<br>395 | His | Cys | Gln | Ala | Pro<br>400 |
| Lys | Ala | Cys | Gln | Val<br>405 | Ala | His | Cys | Ala | Ser<br>410 | Ser | Arg | Gln | Ile | Ile<br>415 | Ser |
| His | Trp | Lys | Asn<br>420 | Cys | Thr | Arg | His | Asp<br>425 | Cys | Pro | Val | Cys | Leu<br>430 | Pro | Leu |
| Lys | Asn | Ala<br>435 | Ser | Asp | Lys | Arg | Asn<br>440 | Gln | Gln | Thr | Ile | Leu<br>445 | Gly | Ser | Pro |
| Ala | Ser<br>450 | Gly | Ile | Gln | Asn | Thr<br>455 | Ile | Gly | Ser | Val | Gly<br>460 | Ala | Gly | Gln | Gln |
| Asn<br>465 | Ala | Thr | Ser | Leu | Ser<br>470 | Asn | Pro | Asn | Pro | Ile<br>475 | Asp | Pro | Ser | Ser | Met<br>480 |
| Gln | Arg | Ala | Tyr | Ala<br>485 | Ala | Leu | Gly | Leu | Pro<br>490 | Tyr | Met | Asn | Gln | Pro<br>495 | Gln |
| Thr | Gln | Leu | Gln<br>500 | Pro | Gln | Val | Pro | Gly<br>505 | Gln | Gln | Pro | Ala | Gln<br>510 | Pro | Pro |
| Ala | His | Gln<br>515 | Gln | Met | Arg | Thr | Leu<br>520 | Asn | Ala | Leu | Gly | Asn<br>525 | Asn | Pro | Met |
| Ser | Val<br>530 | Pro | Ala | Gly | Gly | Ile<br>535 | Thr | Thr | Asp | Gln | Gln<br>540 | Pro | Pro | Asn | Leu |
| Ile<br>545 | Ser | Glu | Ser | Ala | Leu<br>550 | Pro | Thr | Ser | Leu | Gly<br>555 | Ala | Thr | Asn | Pro | Leu<br>560 |
| Met | Asn | Asp | Gly | Ser<br>565 | Asn | Ser | Gly | Asn | Ile<br>570 | Gly | Ser | Leu | Ser | Thr<br>575 | Ile |
| Pro | Thr | Ala | Ala<br>580 | Pro | Pro | Ser | Ser | Thr<br>585 | Gly | Val | Arg | Lys | Gly<br>590 | Trp | His |
| Glu | His | Val<br>595 | Thr | Gln | Asp | Leu | Arg<br>600 | Ser | His | Leu | Val | His<br>605 | Lys | Leu | Val |
| Gln | Ala<br>610 | Ile | Phe | Pro | Thr | Pro<br>615 | Asp | Pro | Ala | Ala | Leu<br>620 | Lys | Asp | Arg | Arg |
| Met<br>625 | Glu | Asn | Leu | Val | Ala<br>630 | Tyr | Ala | Lys | Lys | Val<br>635 | Glu | Gly | Asp | Met | Tyr<br>640 |
| Glu | Ser | Ala | Asn | Ser<br>645 | Arg | Asp | Glu | Tyr | Tyr<br>650 | His | Leu | Leu | Ala | Glu<br>655 | Lys |
| Ile | Tyr | Lys | Ile<br>660 | Gln | Lys | Glu | Leu | Glu<br>665 | Glu | Lys | Arg | Arg | Thr<br>670 | Arg | Leu |

His Lys Gln Gly Ile Leu Gly Asn Gln Pro Ala Leu Pro Ala Ser Gly
        675                 680                 685
Ala Gln Pro Pro Val Ile Pro Pro Ala Gln Ser Val Arg Pro Pro Asn
        690                 695                 700
Gly Pro Leu Pro Leu Pro Val Asn Arg Met Gln Val Ser Gln Gly Met
705                 710                 715                 720
Asn Ser Phe Asn Pro Met Ser Leu Gly Asn Val Gln Leu Pro Gln Ala
                725                 730                 735
Pro Met Gly Pro Arg Ala Ala Ser Pro Met Asn His Ser Val Gln Met
            740                 745                 750
Asn Ser Met Ala Ser Val Pro Gly Met Ala Ile Ser Pro Ser Arg Met
        755                 760                 765
Pro Gln Pro Pro Asn Met Met Gly Thr His Ala Asn Asn Ile Met Ala
        770                 775                 780
Gln Ala Pro Thr Gln Asn Gln Phe Leu Pro Gln Asn Gln Phe Pro Ser
785                 790                 795                 800
Ser Ser Gly Ala Met Ser Val Asn Ser Val Gly Met Gly Gln Pro Ala
                805                 810                 815
Ala Gln Ala Gly Val Ser Gln Gly Gln Glu Pro Gly Ala Ala Leu Pro
            820                 825                 830
Asn Pro Leu Asn Met Leu Ala Pro Gln Ala Ser Gln Leu Pro Cys Pro
        835                 840                 845
Pro Val Thr Gln Ser Pro Leu His Pro Thr Pro Pro Pro Ala Ser Thr
    850                 855                 860
Ala Ala Gly Met Pro Ser Leu Gln His Pro Thr Ala Pro Gly Met Thr
865                 870                 875                 880
Pro Pro Gln Pro Ala Ala Pro Thr Gln Pro Ser Thr Pro Val Ser Ser
                885                 890                 895
Gly Gln Thr Pro Thr Pro Thr Pro Gly Ser Val Pro Ser Ala Ala Gln
            900                 905                 910
Thr Gln Ser Thr Pro Thr Val Gln Ala Ala Ala Gln Ala Gln Val Thr
        915                 920                 925
Pro Gln Pro Gln Thr Pro Val Gln Pro Pro Ser Val Ala Thr Pro Gln
        930                 935                 940
Ser Ser Gln Gln Gln Pro Thr Pro Val His Thr Gln Pro Pro Gly Thr
945                 950                 955                 960
Pro Leu Ser Gln Ala Ala Ala Ser Ile Asp Asn Arg Val Pro Thr Pro
                965                 970                 975
Ser Thr Val Thr Ser Ala Glu Thr Ser Ser Gln Gln Pro Gly Pro Asp
            980                 985                 990
Val Pro Met Leu Glu Met Lys Thr Glu Val Gln Thr Asp Asp Ala Glu
        995                 1000                1005
Pro Glu Pro Thr Glu Ser Lys Gly Glu Pro Arg Ser Glu Met Met Glu
        1010                1015                1020
Glu Asp Leu Gln Gly Ser Ser Gln Val Lys Glu Glu Thr Asp Thr Thr
1025                1030                1035                1040
Glu Gln Lys Ser Glu Pro Met Glu Val Glu Glu Lys Lys Pro Glu Val
                1045                1050                1055
Lys Val Glu Ala Lys Glu Glu Glu Glu Asn Ser Ser Asn Asp Thr Ala
            1060                1065                1070
Ser Gln Ser Thr Ser Pro Ser Gln Pro Arg Lys Lys Ile Phe Lys Pro
        1075                1080                1085
Glu Glu Leu Arg Gln Ala Leu Met Pro Thr Leu Glu Ala Leu Tyr Arg
        1090                1095                1100

-continued

```
Gln Asp Pro Glu Ser Leu Pro Phe Arg Gln Pro Val Asp Pro Gln Leu
1105                1110                1115                1120

Leu Gly Ile Pro Asp Tyr Phe Asp Ile Val Lys Asn Pro Met Asp Leu
                1125                1130                1135

Ser Thr Ile Lys Arg Lys Leu Asp Thr Gly Gln Tyr Gln Glu Pro Trp
                1140                1145                1150

Gln Tyr Val Asp Asp Val Arg Leu Met Phe Asn Asn Ala Trp Leu Tyr
            1155                1160                1165

Asn Arg Lys Thr Ser Arg Val Tyr Lys Phe Cys Ser Lys Leu Ala Glu
            1170                1175                1180

Val Phe Glu Gln Glu Ile Asp Pro Val Met Gln Ser Leu Gly Tyr Cys
1185                1190                1195                1200

Cys Gly Arg Lys Tyr Glu Phe Ser Pro Gln Thr Leu Cys Cys Tyr Gly
                1205                1210                1215

Lys Gln Leu Cys Thr Ile Pro Arg Asp Ala Ala Tyr Tyr Ser Tyr Gln
                1220                1225                1230

Asn Arg Tyr His Phe Cys Gly Lys Cys Phe Thr Glu Ile Gln Gly Glu
                1235                1240                1245

Asn Val Thr Leu Gly Asp Asp Pro Ser Gln Pro Gln Thr Thr Ile Ser
            1250                1255                1260

Lys Asp Gln Phe Glu Lys Lys Asn Asp Thr Leu Asp Pro Glu Pro
1265                1270                1275                1280

Phe Val Asp Cys Lys Glu Cys Gly Arg Lys Met His Gln Ile Cys Val
                1285                1290                1295

Leu His Tyr Asp Ile Ile Trp Pro Ser Gly Phe Val Cys Asp Asn Cys
            1300                1305                1310

Leu Lys Lys Thr Gly Arg Pro Arg Lys Glu Asn Lys Phe Ser Ala Lys
            1315                1320                1325

Arg Leu Gln Thr Thr Arg Leu Gly Asn His Leu Glu Asp Arg Val Asn
    1330                1335                1340

Lys Phe Leu Arg Arg Gln Asn His Pro Glu Ala Gly Glu Val Phe Val
1345                1350                1355                1360

Arg Val Val Ala Ser Ser Asp Lys Thr Val Glu Val Lys Pro Gly Met
                1365                1370                1375

Lys Ser Arg Phe Val Asp Ser Gly Glu Met Ser Glu Ser Phe Pro Tyr
            1380                1385                1390

Arg Thr Lys Ala Leu Phe Ala Phe Glu Glu Ile Asp Gly Val Asp Val
            1395                1400                1405

Cys Phe Phe Gly Met His Val Gln Asp Thr Ala Leu Ile Ala Pro His
    1410                1415                1420

Gln Ile Gln Gly Cys Val Tyr Ile Ser Tyr Leu Asp Ser Ile His Phe
1425                1430                1435                1440

Phe Arg Pro Arg Cys Leu Arg Thr Ala Val Tyr His Glu Ile Leu Ile
                1445                1450                1455

Gly Tyr Leu Glu Tyr Val Lys Lys Leu Val Tyr Val Thr Ala His Ile
            1460                1465                1470

Trp Ala Cys Pro Pro Ser Glu Gly Asp Asp Tyr Ile Phe His Cys His
            1475                1480                1485

Pro Pro Asp Gln Lys Ile Pro Lys Pro Lys Arg Leu Gln Glu Trp Tyr
            1490                1495                1500

Lys Lys Met Leu Asp Lys Ala Phe Ala Glu Arg Ile Ile Asn Asp Tyr
1505                1510                1515                1520

Lys Asp Ile Phe Lys Gln Ala Asn Glu Asp Arg Leu Thr Ser Ala Lys
```

```
                              1525                  1530                  1535
      Glu Leu Pro Tyr Phe Glu Gly Asp Phe Trp Pro Asn Val Leu Glu Glu
                      1540                  1545                  1550
      Ser Ile Lys Glu Leu Glu Gln Glu Glu Glu Arg Lys Lys Glu Glu
                      1555                  1560                  1565
      Ser Thr Ala Ala Ser Glu Thr Pro Glu Gly Ser Gln Gly Asp Ser Lys
                      1570                  1575                  1580
      Asn Ala Lys Lys Lys Asn Asn Lys Lys Thr Asn Lys Asn Lys Ser Ser
      1585                  1590                  1595                  1600
      Ile Ser Arg Ala Asn Lys Lys Lys Pro Ser Met Pro Asn Val Ser Asn
                      1605                  1610                  1615
      Asp Leu Ser Gln Lys Leu Tyr Ala Thr Met Glu Lys His Lys Glu Val
                      1620                  1625                  1630
      Phe Phe Val Ile His Leu His Ala Gly Pro Val Ile Ser Thr Gln Pro
                      1635                  1640                  1645
      Pro Ile Val Asp Pro Asp Pro Leu Leu Ser Cys Asp Leu Met Asp Gly
                      1650                  1655                  1660
      Arg Asp Ala Phe Leu Thr Leu Ala Arg Asp Lys His Trp Glu Phe Ser
      1665                  1670                  1675                  1680
      Ser Leu Arg Arg Ser Lys Trp Ser Thr Leu Cys Met Leu Val Glu Leu
                      1685                  1690                  1695
      His Thr Gln Gly Gln Asp Arg Phe Val Tyr Thr Cys Asn Glu Cys Lys
                      1700                  1705                  1710
      His His Val Glu Thr Arg Trp His Cys Thr Val Cys Glu Asp Tyr Asp
                      1715                  1720                  1725
      Leu Cys Ile Asn Cys Tyr Asn Thr Lys Ser His Thr His Lys Met Val
                      1730                  1735                  1740
      Lys Trp Gly Leu Gly Leu Asp Asp Glu Gly Ser Ser Gln Gly Glu Pro
      1745                  1750                  1755                  1760
      Gln Ser Lys Ser Pro Gln Glu Ser Arg Arg Leu Ser Ile Gln Arg Cys
                      1765                  1770                  1775
      Ile Gln Ser Leu Val His Ala Cys Gln Cys Arg Asn Ala Asn Cys Ser
                      1780                  1785                  1790
      Leu Pro Ser Cys Gln Lys Met Lys Arg Val Val Gln His Thr Lys Gly
                      1795                  1800                  1805
      Cys Lys Arg Lys Thr Asn Gly Gly Cys Pro Val Cys Lys Gln Leu Ile
                      1810                  1815                  1820
      Ala Leu Cys Cys Tyr His Ala Lys His Cys Gln Glu Asn Lys Cys Pro
      1825                  1830                  1835                  1840
      Val Pro Phe Cys Leu Asn Ile Lys His Asn Val Arg Gln Gln Gln Ile
                      1845                  1850                  1855
      Gln His Cys Leu Gln Gln Ala Gln Leu Met Arg Arg Arg Met Ala Thr
                      1860                  1865                  1870
      Met Asn Thr Arg Asn Val Pro Gln Gln Ser Leu Pro Ser Pro Thr Ser
                      1875                  1880                  1885
      Ala Pro Pro Gly Thr Pro Thr Gln Gln Pro Ser Thr Pro Gln Thr Pro
                      1890                  1895                  1900
      Gln Pro Pro Ala Gln Pro Gln Pro Ser Pro Val Asn Met Ser Pro Ala
      1905                  1910                  1915                  1920
      Gly Phe Pro Asn Val Ala Arg Thr Gln Pro Pro Thr Ile Val Ser Ala
                      1925                  1930                  1935
      Gly Lys Pro Thr Asn Gln Val Pro Ala Pro Pro Pro Pro Ala Gln Pro
                      1940                  1945                  1950
```

```
Pro Pro Ala Ala Val Glu Ala Ala Arg Gln Ile Glu Arg Glu Ala Gln
        1955                1960                1965
Gln Gln Gln His Leu Tyr Arg Ala Asn Ile Asn Asn Gly Met Pro Pro
        1970                1975                1980
Gly Arg Asp Gly Met Gly Thr Pro Gly Ser Gln Met Thr Pro Val Gly
1985                1990                1995                2000
Leu Asn Val Pro Arg Pro Asn Gln Val Ser Gly Pro Val Met Ser Ser
                2005                2010                2015
Met Pro Pro Gly Gln Trp Gln Gln Ala Pro Ile Pro Gln Gln Gln Pro
        2020                2025                2030
Met Pro Gly Met Pro Arg Pro Val Met Ser Met Gln Ala Gln Ala Ala
        2035                2040                2045
Val Ala Gly Pro Arg Met Pro Asn Val Gln Pro Asn Arg Ser Ile Ser
        2050                2055                2060
Pro Ser Ala Leu Gln Asp Leu Leu Arg Thr Leu Lys Ser Pro Ser Ser
2065                2070                2075                2080
Pro Gln Gln Gln Gln Gln Val Leu Asn Ile Leu Lys Ser Asn Pro Gln
                2085                2090                2095
Leu Met Ala Ala Phe Ile Lys Gln Arg Thr Ala Lys Tyr Val Ala Asn
        2100                2105                2110
Gln Pro Gly Met Gln Pro Gln Pro Gly Leu Gln Ser Gln Pro Gly Met
        2115                2120                2125
Gln Pro Gln Pro Gly Met His Gln Gln Pro Ser Leu Gln Asn Leu Asn
        2130                2135                2140
Ala Met Gln Ala Gly Val Pro Arg Pro Gly Val Pro Pro Pro Gln Pro
2145                2150                2155                2160
Ala Met Gly Gly Leu Asn Pro Gln Gly Gln Ala Leu Asn Ile Met Asn
        2165                2170                2175
Pro Gly His Asn Pro Asn Met Thr Asn Met Asn Pro Gln Tyr Arg Glu
        2180                2185                2190
Met Val Arg Arg Gln Leu Leu Gln His Gln Gln Gln Gln Gln Gln Gln
        2195                2200                2205
Gln Gln Gln Gln Gln Gln Gln Gln Asn Ser Ala Ser Leu Ala Gly Gly
        2210                2215                2220
Met Ala Gly His Ser Gln Phe Gln Gln Pro Gln Gly Pro Gly Gly Tyr
2225                2230                2235                2240
Ala Pro Ala Met Gln Gln Gln Arg Met Gln Gln His Leu Pro Ile Gln
                2245                2250                2255
Gly Ser Ser Met Gly Gln Met Ala Ala Pro Met Gly Gln Leu Gly Gln
                2260                2265                2270
Met Gly Gln Pro Gly Leu Gly Ala Asp Ser Thr Pro Asn Ile Gln Gln
        2275                2280                2285
Ala Leu Gln Gln Arg Ile Leu Gln Gln Gln Met Lys Gln Gln Ile
        2290                2295                2300
Gly Ser Pro Gly Gln Pro Asn Pro Met Ser Pro Gln Gln His Met Leu
2305                2310                2315                2320
Ser Gly Gln Pro Gln Ala Ser His Leu Pro Gly Gln Gln Ile Ala Thr
                2325                2330                2335
Ser Leu Ser Asn Gln Val Arg Ser Pro Ala Pro Val Gln Ser Pro Arg
        2340                2345                2350
Pro Gln Ser Gln Pro Pro His Ser Ser Pro Ser Pro Arg Ile Gln Pro
        2355                2360                2365
Gln Pro Ser Pro His His Val Ser Pro Gln Thr Gly Thr Pro His Pro
        2370                2375                2380
```

```
Gly Leu Ala Val Thr Met Ala Ser Ser Met Asp Gln Gly His Leu Gly
2385                2390                2395                2400

Asn Pro Glu Gln Ser Ala Met Leu Pro Gln Leu Asn Thr Pro Asn Arg
            2405                2410                2415

Ser Ala Leu Ser Ser Glu Leu Ser Leu Val Gly Asp Thr Thr Gly Asp
            2420                2425                2430

Thr Leu Glu Lys Phe Val Glu Gly Leu
            2435                2440
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

```
Lys Val Glu Gly Asp Met Tyr Glu Ser Ala Asn Ser Arg Asp Glu
1               5                   10                  15
```

ASSAYS FOR THE IDENTIFICATION OF COMPOUNDS WHICH INHIBIT ACTIVATION OF CAMP AND MITOGEN RESPONSIVE GENES

This invention was made in part with Government support under Grant No. GM 37828 provided by the National Institutes of Health. The Government may have certain rights in this invention.

FIELD OF THE INVENTION

The present invention relates to analytical methods. In a particular aspect, the present invention relates to methods for the identification of compounds which mediate the interaction between signal dependent transcription factors and co-factor protein(s) involved in the activation of transcription. In another aspect, the present invention relates to methods for the identification of new signal dependent transcription factors. In yet another aspect, the present invention relates to methods for the identification of novel co-factor protein(s) which mediate the interaction between signal dependent transcription factors and inducer molecules involved in the activation of transcription.

BACKGROUND OF THE INVENTION

Many eukaryotic genes are regulated in an inducible, cell type-specific fashion. Genes expressed in response to heat shock, steroid/thyroid hormones, phorbol esters, cyclic adenosine monophosphate (cAMP), growth factors and heavy metal ions are examples of this class. The activity of cells is controlled by external signals that stimulate or inhibit intracellular events. The process by which an external signal is transmitted into and within a cell to elicit an intracellular response is referred to as signal transduction. Signal transduction is generally initiated by the interaction of extracellular factors (or inducer molecules, i.e., growth factors, hormones, adhesion molecules, neurotransmitters, and other mitogens) with receptors at the cell surface. Extracellular signals are transduced to the inner face of the cell membrane, where the cytoplasmic domains of receptor molecules contact intracellular targets. The initial receptor-target interactions stimulate a cascade of additional molecular interactions involving multiple intracellular pathways that disseminate the signal throughout the cell.

Many of the proteins involved in signal transduction contain multiple domains. Some of these domains have enzymatic activity and some of these domains are capable of binding to other cellular proteins, DNA regulatory elements, calcium, nucleotides, lipid mediators, and the like.

Protein-protein interactions are involved in all stages of the intracellular signal transduction process-at the cell membrane, where the signal is initiated in the cytoplasm by receptor recruitment of other cellular proteins, in the cytoplasm where the signals are disseminated to different cellular locations, and in the nucleus where proteins involved in transcriptional control congregate to turn on or turn off gene expression.

Mitogenic signaling affects the transcriptional activation of specific sets of genes and the inactivation of others. The nuclear effectors of gene activation are transcription factors that bind to DNA as homomeric or heteromeric dimers. Phosphorylation also modulates the function of transcription factors, as well. Oncogenes, first identified as the acute transforming genes transduced by retroviruses, are a group of dominantly acting genes. Such genes, which are involved in cell division, encode growth factors and their receptors, as well as second messengers and mitogenic nuclear proteins activated by growth factors.

The binding of growth factors to their respective receptors activates a cascade of intracellular pathways that regulate phospholipid metabolism, arachidonate metabolism, protein phosphorylation, calcium mobilization and transport, and transcriptional regulation. Specific phosphorylation events mediated by protein kinases and phosphatases modulate the activity of a variety of transcription factors within the cell. These signaling events can induce changes in cell shape, mobility, and adhesiveness, or stimulate DNA synthesis. Aberrations in these signal-induced events are associated with a variety of hyperproliferative diseases ranging from cancer to psoriasis.

The ability to repress intracellular signal-induced response pathways is an important mechanism in negative control of gene expression. Selective disruption of such pathways would allow the development of therapeutic agents capable of treating a variety of disease states related to improper activation and/or expression of specific transcription factors. The present invention satisfies this need and provides related advantages as well.

SUMMARY OF THE INVENTION

In accordance with the present invention, it has been discovered that cAMP-response-element-binding protein (also referred to as CREB binding protein or CBP) cooperates with upstream activators involved in the activation of transcription by signal dependent transcription factors, such as c-Jun (responsive to phorbol ester), serum response factor, and the like. Accordingly, assays employing CBP have been developed for the identification of compounds which disrupt the ability of signal dependent transcription factors to activate transcription. In another aspect, assays employing CBP have been developed for the identification of new signal dependent transcription factors. In yet another aspect of the present invention, assays employing CBP have been developed for the identification of novel co-factor protein(s) which mediate the interaction between signal dependent transcription factors and inducer molecules involved in the activation of transcription. In still another aspect, an assay is provided to identify compounds which have the binding and/or activation properties characteristic of CREB binding protein.

DETAILED DESCRIPTION OF THE INVENTION

Figure 1:
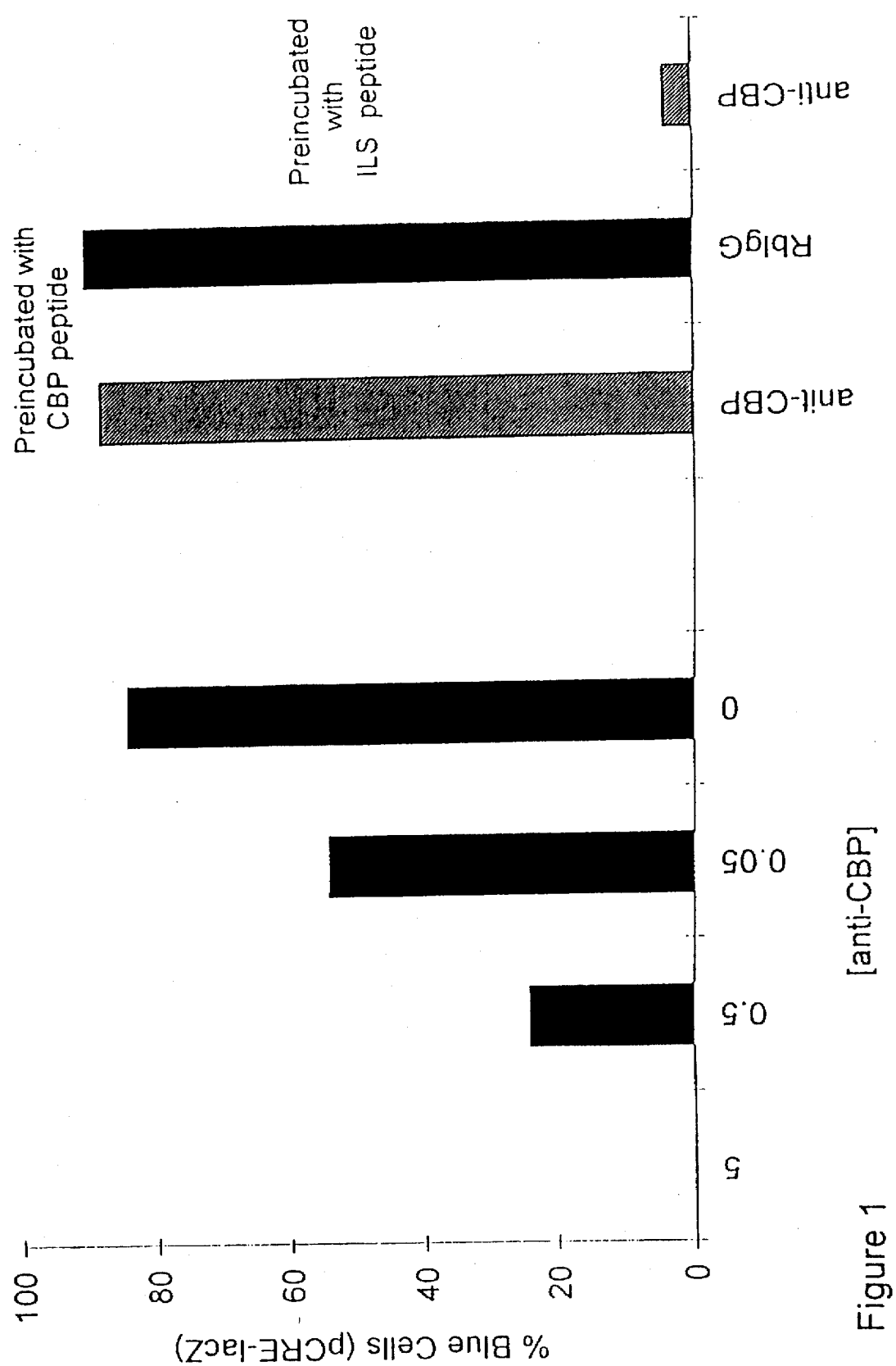
FIG. 1 is a bar graph summarizing the injections described in Example 2. Each bar represents the percentage of positive cells expressing β-galactosidase from 2–3 experiments where 100–200 cells were injected in each experiment. denotes concentration of affinity purified CBP antiserum injected into cells. Right (hatched bars) indicate the percent lacZ positive cells after microinjection of CRE-lacZ (camp responsive element-lac operon β-galactosidase) reporter with CBP antiserum (anti-CBP) or control IgG (RbIgG). Preincubation of antisera with CBP peptide or non-specific ILS peptide (1mg/ml) was carried out as indicated.

Cyclic AMP (cAMP) regulates the transcription of numerous genes through protein kinase-A (PK-A) mediated phosphorylation, at Ser133, of transcription factor CREB. Within the CREB protein, a 60 amino acid Kinase Inducible Domain (KID) mediates transcriptional induction by PK-A. Based on recent work describing a nuclear CREB Binding Protein (CBP), which specifically interacts with the phosphorylated KID domain of CREB, it has been examined whether CBP is necessary for cAMP regulated transcription. Antisera against CBP have been found to completely inhibit transcription from a cAMP responsive promoter, but not from constitutively active promoters. Surprisingly, CBP has also been found to cooperate with upstream activators involved in phorbol ester and serum responsive transcription. It is demonstrated herein that recruitment of CBP to certain inducible promoters is intimately involved in transmitting inductive signals from phosphorylated, and thus activated, upstream factors to the RNA polymerase II complex. A number of analytical uses for CBP and CBP-like compounds based on these observations are described herein.

In accordance with the present invention, there is provided a method for the identification of a compound which inhibits activation of cAMP and mitogen responsive genes, said method comprising:

monitoring expression of reporter in response to exposure to said compound, relative to expression of reporter in the absence of said compound, wherein exposure to said compound is carried out in the presence of:
  a signal dependent transcription factor,
  a polypeptide comprising at least amino acid residues 461–661 of the protein set forth in SEQ ID NO:2, and
  a reporter construct comprising a reporter gene under the control of said signal dependent transcription factor.

As employed herein, the phrase "cAMP and mitogen responsive genes" refers to early response genes which are activated in response to a diverse array of agents including mitogens, such as, growth factors, differentiation inducers and biomodulators. Examples of such agents include insulin-like growth factor (IGF-1), erythropoietin (EPO), nerve growth factor (NGF), epidermal growth factor (EGF), platelet-derived growth factor (PDGF), fibroblast growth factor (FGF), transforming growth factor β (TGFβ), interferon, tumor necrosis factor (TNF), interleukins, granulocyte-macrophage colony-stimulating factor (GM-CSF), G-CSF, prolactin, serotonin, angiotensin, bombesin, bradykinin, noradrenalin, putrescine, concanavalin A, various oncogenic agents including tumor viruses, UV irradiation, estrogen, progesterone, testosterone, and the like.

Signal dependent transcription factors contemplated for use in the practice of the present invention include phosphorylation dependent activators such as Jun, Fos, and other early response genes such as Myc, Myb, erbA, and Rel, serum responsive factor, Elk, as well as steroid hormone receptors (e.g., glucocorticoid receptor (GR)), and the like.

Polypeptides employed in the invention assay function as co-factors by binding to the signal dependent transcription factor as a necessary component of a transcriptionally active complex. Examples of such co-factors include CBP (i.e., substantially the entire amino acid sequence set forth in SEQ ID NO:2), a polypeptide comprising amino acid residues 1–661 as set forth in SEQ ID NO:2, as well as functional fragments thereof, e.g., residues 461–661, and homologues thereof, such as those identified by the method described herein for the identification of compounds which have the binding and/or activation properties characteristic of CREB binding protein. In accordance with one embodiment of the present invention, there are provided purified and isolated polypeptides, CBPs, that bind to a specific sequence within phosphorylated CREB.

As used herein, the term "purified" means that the molecule is substantially free of contaminants normally associated with a native or natural environment. CREB binding protein, or functional fragments thereof, useful in the practice of the present invention, can be obtained by a number of methods, e.g., precipitation, gel filtration, ion-exchange, reversed-phase, DNA affinity chromatography, and the like. Other well-known methods are described in Deutscher et al., *Guide to Protein Purification: Methods in Enzymology* Vol. 182, (Academic Press, 1990), which is incorporated herein by reference.

Alternatively, a purified CBP, or functional fragment thereof, useful in the practice of the present invention, can also be obtained by well-known recombinant methods as described, for example, in Ausubel et al., *Current Protocols in Molecular Biology* (Greene Publishing Associates, Inc. and John Wiley & Sons, Inc. 1993), also incorporated herein by reference. An example of recombinant means to prepare CBP, or functional fragments thereof, is to express nucleic acid encoding CBP, or functional fragment thereof, in a suitable host cell, such as a bacterial, yeast or mammalian cell, using methods well known in the art, and recovering the expressed protein, again using methods well known in the art.

CBPs, and biologically active fragments thereof, useful in the practice of the present invention can also be produced by chemical synthesis. Synthetic polypeptides can be produced using Applied Biosystems, Inc. Model 430A or 431A automatic polypeptide synthesizer and chemistry provided by the manufacturer. CBP, and biologically active fragments thereof, can also be isolated directly from cells which have been transformed with the expression vectors described below in more detail.

The present invention also encompasses nucleic acids encoding CBP and functional fragments thereof. See, for example, SEQ ID NO:1. This invention also encompasses nucleic acids which encode substantially the entire amino acid sequence set forth in SEQ ID NO:2 (for example, the nucleic acid sequence set forth in SEQ ID NO:1, as well as nucleic acid sequences which differ from that set forth in SEQ ID NO:1 due to the degeneracy of the genetic code), nucleic acids which encode amino acid residues 1–661, as set forth in SEQ ID NO:2, nucleic acids which encode amino acid residues 461–661, as set forth in SEQ ID NO:2, as well as nucleic acids which encode substantially the same amino acid sequences as any of those referred to above, but which differ only by the presence of conservative amino acid changes that do not alter the binding and/or activation properties of the CBP or CBP-like polypeptide encoded thereby.

The invention further provides the above-described nucleic acids operatively linked to a promoter, as well as other regulatory sequences. As used herein, the term "operatively linked" means positioned in such a manner that the promoter will direct the transcription of RNA from the nucleic acid. Examples of such promoters are SP6, T4 and T7.

Vectors which contain both a promoter and a cloning site into which a piece of DNA can be inserted so as to be operatively linked to the promoter are well known in the art. Preferably, these vectors are capable of transcribing RNA in vitro or in vivo. Examples of such vectors are the pGEM series (Promega Biotech, Madison, Wis.). This invention also provides a vector comprising a nucleic acid molecule such as DNA, cDNA or RNA encoding a CBP polypeptide. Examples of additional vectors useful herein are viruses, such as bacteriophages, baculoviruses and retroviruses, cosmids, plasmids, and the like. Nucleic acids are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers that correspond to a restriction site in the vector DNA can be ligated to the insert DNA which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are available and can readily be accessed by those of skill in the art.

Also provided are expression vectors comprising DNA encoding a mammalian CBP, or functional fragment thereof, adapted for expression in a bacterial cell, a yeast cell, a mammalian cell or other animal cell. Such vectors comprise the regulatory elements necessary for expression of the DNA in the bacterial, yeast, mammalian or animal cells. Regulatory elements are positioned relative to the DNA encoding the CBP polypeptide so as to permit expression thereof. Regulatory elements required for expression include promoter sequences to bind RNA polymerase and transcription initiation sequences for ribosome binding. For example, a bacterial expression vector includes a promoter such as the lac promoter and the Shine-Dalgarno sequence and the start codon AUG (Ausubel et al., supra 1993) for transcription initiation. Similarly a eukaryotic expression vector includes a heterologous or homologous promoter for RNA polymerase II, a downstream polyadenylation signal, the start codon AUG, and a termination codon for detachment of the ribosome. Such vectors can readily be obtained commercially or assembled by methods well known in the art, for example, the methods described above for constructing vectors in general. Expression vectors are useful to produce cells that express CBP or functional fragments thereof.

As employed herein, the term "reporter construct" refers to a recombinant construct, for example, an expression vector comprising a reporter gene under the control of a signal dependent transcription factor. A signal which induces activation or inactivation of a target gene induces the reporter gene to express an exogenous identifiable "signal". Expression of the reporter gene indicates that the target gene has been modulated. Exemplary reporter genes encode luciferase, β-galactosidase, chloramphenicol transferase, and the like. Exemplary reporter constructs useful in the practice of the present invention include CRE-lacZ, SRE-lacZ, TRE-lacZ, and the like.

In practicing the assays of the present invention, reporter plasmid is introduced into suitable host cells, along with CBP or a CBP-like polypeptide (or a DNA construct encoding same) and signal dependent transcription factor. The transfected host cells are then cultured in the presence and absence (as a control) of test compound suspected of being capable of inhibiting activation of cAMP and mitogen responsive genes. Next the transfected and cultured host cells are monitored for induction (i.e., the presence) of the product of the reporter gene.

Any cell line can be used as a suitable "host" for the invention assays. Presently preferred host cells for use in invention assays are HeLa and NIH3T3 cells.

In accordance with the present invention, expression of the reporter gene can be monitored in a variety of ways. Immunological procedures useful for in vitro detection of a polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

Compounds which are capable of inhibiting activation of cAMP and mitogen responsive genes, and hence can be identified by the invention assay method, include antibodies raised against the binding domain of the protein set forth in SEQ ID NO:2, antibodies raised against the binding domain of CBP-like compounds, and the like. Presently preferred antibodies are those raised against a polypeptide fragment comprising amino acid residues from about 461 up to 661 of the protein set forth in SEQ ID NO:2; with antibodies raised against a polypeptide fragment comprising amino acid residues from about 634 up to 648 of the protein set forth in SEQ ID NO:2 (this subfragment is also set forth specifically as SEQ ID NO:3) being especially preferred.

Antibodies contemplated for use in the practice of the present invention have specific reactivity with the above-described CBP or CBP-like compounds. Active antibody fragments are encompassed within the definition of "antibody." As used herein "specific reactivity" refers to the ability of an antibody to recognize and bind to an epitope on CBP or CBP-like compounds. Antibodies employed in the practice of the present invention can be produced by any method known in the art. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The above-described CBP or CBP-like compounds can be used as the immunogen in generating such antibodies. Altered antibodies, such as chimeric, humanized, CDR-grafted or bifunctional antibodies can also be produced by methods well known to those skilled in the art. Such antibodies can also be produced by hybridoma, chemical or recombinant methodology described, for example in Ausubel et al., supra. The antibodies can be used for determining the presence of a CBP-derived polypeptide, for the purification of CBP-derived polypeptides, for in vitro diagnostic methods, and the like.

In accordance with another embodiment of the present invention, there is provided a method for the identification of a compound which inhibits activation of cAMP and mitogen responsive genes, said method comprising:

(1) contacting a test system with said compound under physiological conditions; and (2) monitoring expression of reporter in response to said compound, relative to expression of reporter in the absence of said compound, wherein said reporter is encoded by a reporter construct comprising a reporter gene under the control of a signal dependent transcription factor, and wherein said test system comprises:
said signal dependent transcription factor,
a polypeptide comprising at least amino acid residues 461–661 of the protein set forth in SEQ ID NO:2, and
said reporter construct.

In accordance with yet another embodiment of the present invention, there is provided a method for the identification of a compound which promotes activation of cAMP and mitogen responsive genes, said method comprising:

monitoring expression of reporter in response to exposure to said compound, relative to expression of reporter in the absence of said compound, wherein exposure to said compound is carried out in the presence of:
a signal dependent transcription factor, or
a polypeptide comprising at least amino acid residues 461–661 of the protein set forth in SEQ ID NO:2, and
a reporter construct;

wherein said reporter construct comprises a reporter gene under the control of a signal dependent transcription factor.

In accordance with still another embodiment of the present invention, there is provided a method for the identification of a compound which has the binding and/or activation properties characteristic of CREB binding protein, said method comprising:

monitoring expression of reporter in response to exposure to said compound, relative to expression of reporter in the absence of said compound, wherein exposure to said compound is carried out in the presence of:
a signal dependent transcription factor, and
a reporter construct, wherein said reporter construct comprises a reporter gene under the control of a signal dependent transcription factor.

In accordance with a still further embodiment of the present invention, there is provided a method for the identification of a compound which has the transcription activation properties characteristic of a signal dependent transcription factor, said method comprising:

monitoring expression of reporter in response to exposure to said compound, relative to expression of reporter in the absence of said compound, wherein exposure to said compound is carried out in the presence of:
a polypeptide comprising at least amino acid residues 461–661 of the protein set forth in SEQ ID NO:2, and
a reporter construct, wherein said reporter construct comprises a reporter gene under the control of a signal dependent transcription factor.

The invention will now be described in greater detail by reference to the following non-limiting examples.

EXAMPLE I

Functional Properties of CBP

To characterize the functional properties of CBP, rabbit CBP antiserum was developed against a fragment of CBP extending from amino acid residues 634–648 within the CREB binding domain of CBP (i.e., KVEGDMYESAN-SRDE; SEQ ID NO:3). Crude antiserum was affinity purified on a synthetic CBP peptide column, as described by Gonzalez et al., in Mol. and Cell Biol. 11(3):1306–1312 (1991), which is incorporated herein by reference. Far-Western and Western blot assays were performed as described by, for example, Chrivia et al., in Nature 365:855–859 (1993), also incorporated herein by reference. Thus, Western (CBP) and Far-Western ($^{32}$P-CREB) blot analysis of partially purified CBP protein from HeLa nuclear extract was carried out following SDS-PAGE and transfer to nitrocellulose. Far-Western blots were also obtained for crude HeLa nuclear extracts using $^{32}$P-labeled CREB, phosphorylated with PK-A or casein kinase II (CKII). Far-Western blot analysis was also conducted with immunoprecipitates prepared from HeLa nuclear extracts with control IgG or affinity purified CBP antiserum (CBP-Ab). CREB binding activity was detected with $^{32}$P-labeled CREB phosphorylated with PK-A.

Using the above-described antiserum, a 265 kD polypeptide was detected on Western blots, as predicted from the cDNA (see Chrivia et al., supra), which coincided with the predominant phospho-CREB binding activity in HeLa nuclear extracts by "Far-Western" blot assay. An identical phospho-CREB binding activity was also found in NIH3T3 cells. This phospho-CREB binding protein appeared to be specific for Ser133 phosphorylated CREB because no such band was detected with CREB labeled to the same specific activity at a non-regulatory phospho-acceptor site (Ser156) by casein kinase II (CKII) (see Hagiwara et al., Cell 70:105–113 (1992), which is incorporated herein by reference).

To further demonstrate that the major phospho-CREB binding protein in HeLa and NIH3T3 cells is specifically bound by the anti-CBP antibody, immunoprecipitates were prepared from crude nuclear extracts using the CBP antiserum. Far-Western analysis of these immunoprecipitates revealed a 265 kD band in samples incubated with CBP antiserum, but not with control IgG.

EXAMPLE II

Role of Phosphorylation in CREB-CBP Interaction

To examine whether the phosphorylation dependent interaction between CREB and CBP was critical for cAMP responsive transcription, a microinjection assay was employed using CBP antiserum, which would be predicted to impair formation of a CREB-CBP complex. Thus, NIH3T3 cells were cultured in 5% $CO_2$ atmosphere in Dulbecco's Modified Eagle's Medium (DMEM), supplemented with 10% fetal calf serum. Forty-eight hours prior to injection, cells were passaged into scored glass coverslips and made quiescent by incubation in medium containing 0.05% fetal calf serum for 24 hours (see, for example, Hagikara et al., supra and Alberts et al., in Mol. and Cell Biol. 13:2104–2112 (1993), both incorporated herein by reference). Representative fields of NIH3T3 cells were injected with pCRE-lacZ reporter plasmid plus 5, 0.5, and 0.05 mg/ml of affinity purified CBP antiserum. Total antibody concentration in microinjected cells was maintained at 5 mg/ml by adjusting with control Rabbit IgG. Injected cells were stimulated with 0.5 mM 8-bromo-cAMP, plus 3-isobutyl-1-methylxanthine (IBMX) for 4 hours, then fixed and assayed for lacZ activity (β-Gal) as well as antibody content (Texas Red anti-Rb).

Following microinjection into nuclei of NIH3T3 cells, a CRE-lacZ reporter was markedly induced by treatment with 8-bromo-cAMP plus IBMX. Co-injection of CBP antiserum with the CRE-lacZ plasmid inhibited cAMP dependent activity in a dosage-dependent manner, but control IgG had no effect on this response.

To determine whether CBP antiserum inhibited cAMP responsive transcription by binding specifically to CBP, peptide blocking experiments were performed. Thus, the effect of CBP antiserum on CRE-lacZ reporter activity following pre-treatment of CBP antiserum with synthetic CBP peptide (anti-CBP+CBP) or unrelated peptide (anti-CBP+ILS; the unrelated peptide, ILS, is described by Leonard et al., in Mol. Endocr. 7: 1275–1283 (1993), which is incorporated herein by reference) was determined. Rabbit IgG+CBP and rabbit IgG pre-treated with CBP peptide were used as controls. NIH3T3 cells were injected with CRE-lacZ reporter plus various CBP antisera, stimulated with 0.5 mM 8-bromo-cAMP, plus IBMX for 4 hours, and assayed for lacZ activity. Cells expressing the lacZ gene product form a blue precipitate upon X-gal staining, which quenches immunofluorescent detection of the injected antibody.

CBP antiserum, pre-incubated with synthetic CBP peptide, was unable to recognize the 265 kD CBP product on a Western blot, and could not inhibit CRE-lacZ reporter activity upon microinjection into NIH3T3 cells. But antiserum treated with an unrelated synthetic peptide (ILS) retained full activity in both Western and microinjection assay, suggesting that the ability of the antiserum to bind CBP was critical for its inhibitory effect on cAMP dependent transcription.

Results of these experiments are summarized in FIG. 1.

EXAMPLE III

Multiple Signalling Pathways Utilize CBP

To determine whether CBP activity may be restricted to a subset of promoters, several constitutively active reporter constructs were tested:

Cytomegalovirus (CMV-lacZ),

Rous sarcoma virus (RSV-IacZ), and

Figure 2:
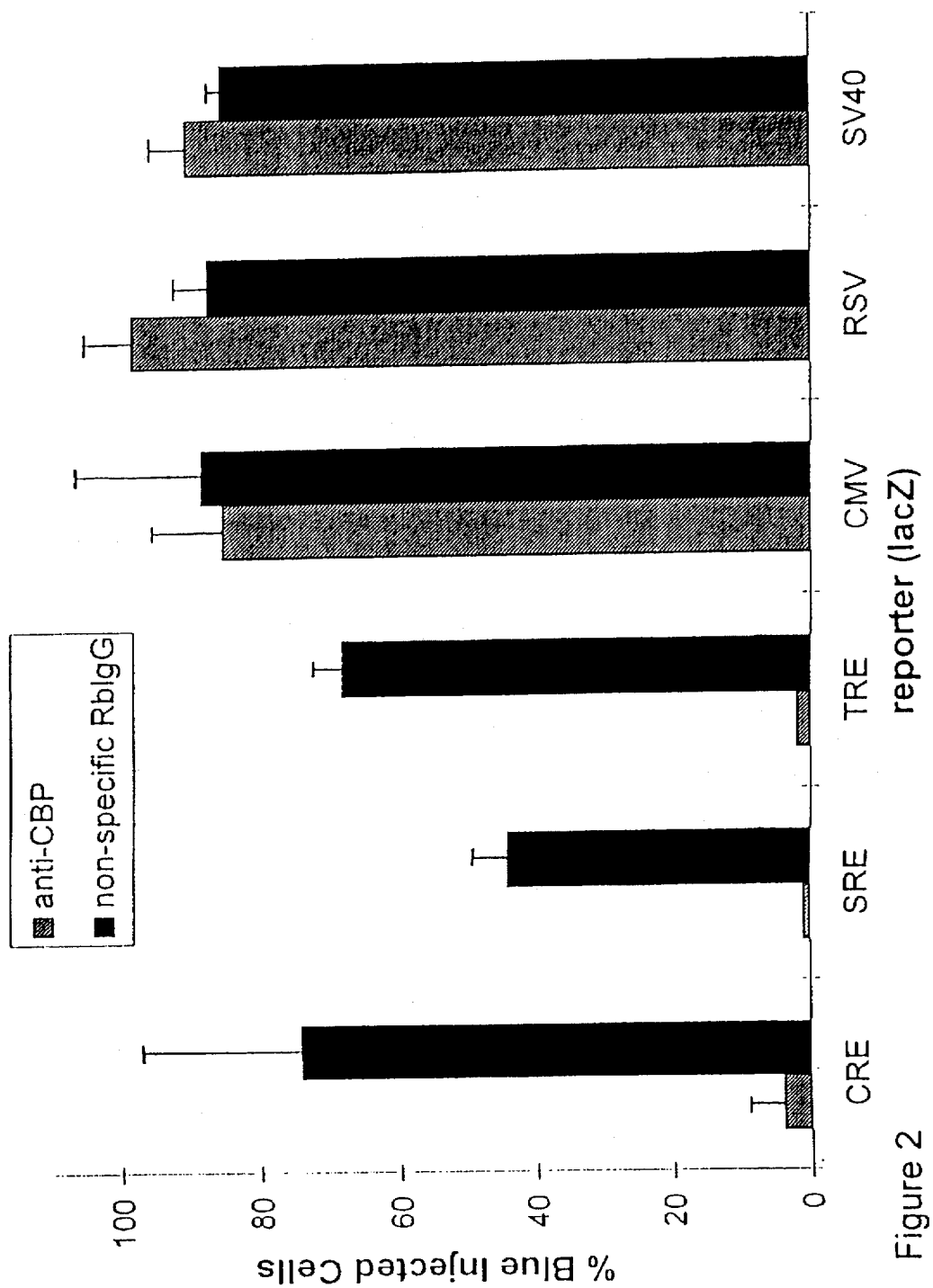
FIG. 2 is a bar graph summarizing the results of CBP antisera injections, as described in Example 3. Bars represent the percentage of lacZ positive (blue) cells (mean ±standard deviation) from 3–5 experiments where 100–200 cells were injected in each experiment. Injected cells were identified by immunofluorescence and/or lacZ staining. Reporter plasmid encoding the lacZ reporter was microinjected into NIH3T3 cells. CRE-lacZ, SRE-lacZ (serum responsive element-lac operon β-galactosidase) TRE-lacZ (TPA responsive element-lac operon β-galactosidase) reporter activities were determined after microinjected cells were treated as described herein. CMV-lacZ (Cytomegalovirus-lac operon β-gakactisudase), RSV-lacZ (Rous sarcoma virus-lac operon β-galactosidase) and SV40-lacZ (simian virus 40-lac operon β-galactosidase) reporter activities were measured in the absence of inducers. Hatched bars indicate % blue cells after microinjection with CBP antiserum. Solid bars indicate % blue cells following injection with control rabbit IgG (RbIgG).

SV40 (SV40-lacZ). Thus, cells were microinjected with CBP antiserum plus Rous Sarcoma Virus (pRSV-lacZ) or Cytomegalovirus (pCMV-lacZ) reporter constructs. Alternatively, NIH3T3 cells microinjected with CBP antiserum (or non-specific rabbit IgG (RbIgG)), plus reporter constructs containing either cAMP responsive elements (pCRE-lacZ), serum responsive elements (pSRE-lacZ) or phorbol ester responsive elements (pTRE-lacZ). Light field photo-micrographs show cells stained for β-galactosidase activity following four hour treatment with either 0.5 mM 8-bromo-cAMP, plus IBMX (pCRE-lacZ), 20% fetal calf serum (pSRE-lacZ), or 200 ng/ml TPA (pTRE-lacZ). Results of β-galactosidase assays are summarized in FIG. 2. Dark field photos show microinjected IgGs as visualized by immunofluorescence using Texas Red donkey anti-rabbit IgG.

When examined in NIH3T3 cells by transient transfection assay, each of the constitutively active reporter constructs had comparable basal activity, relative to the cAMP-stimulated CRE reporter plasmid, thereby permitting the effects of CBP antiserum on these reporters to be compared directly. Although co-injected CBP antiserum could block cAMP stimulated activity from a CRE-lacZ reporter in contemporaneous assays, no inhibition was observed on basal expression from any of the constitutive promoter constructs tested, even when 10-fold lower amounts of reporter plasmid were employed.

These results suggest that CBP can indeed discriminate between basal and signal dependent activities in vivo.

EXAMPLE IV

CBP-involvement in non-CREB mediated pathways

Previous reports showing that serum and phorbol esters stimulate their target genes through phosphorylation-dependent trans-activators (see, for example, Hill et al., in Cell 73:395–406 (1993) or Smeal et al., in Nature 354:494–496 (1991), both incorporated herein by reference), suggested that CBP might also function in these signaling pathways. Thus, Far-Western analyses were carried out with crude HeLa nuclear extracts using $^{32}$p-labeled recombinant Jun protein phosphorylated in vitro with either Jun-kinase (JNK; see Hibi et al., in Genes and Develop. 7:2135–2148 (1993), incorporated herein by reference) or casein kinase II (CK II).

Whereas serum and TPA could stimulate reporter activity in NIH3T3 cells microinjected with serum responsive element (SRE)-lacZ and TPA-responsive element (TRE)-lacZ indicator plasmids, respectively, co-injected CBP antiserum completely blocked both responses. These results suggest that CBP not only interacts with CREB, but also with other signal-dependent transcription factors.

In this regard, phorbol esters and serum induce TRE-dependent transcription, in part, through the Jun-kinase (JNK) mediated phosphorylation of c-Jun at Ser63 and Ser73 (see, for example, Smeal et al., supra or Hibi et al., supra). Using $^{32}$P-labeled recombinant c-Jun protein, phosphorylated at Ser63 and Ser73 with JNK, Far-Western blot assays were performed on crude HeLa nuclear extracts. JNK-phosphorylated c-Jun protein could bind CBP with comparable affinity to CREB. But c-Jun labeled to similar specific activity at non-activating sites (Thr 231, Ser243, and Ser249; see Boyle et al., in Cell 64:573–584 (1991)) by CKII, could not interact with CBP, suggesting that interaction between CBP and c-Jun requires phosphorylation of the transcriptionally active Ser63 and Ser73 phospho-acceptor sites. In view of the inhibitory effect of CBP antiserum on TRE-β gal reporter expression following phorbol ester and serum induction, the phosphorylation dependent interaction between CBP and c-Jun would appear to be a critical component of these response pathways.

EXAMPLE V

Chromatographic purification of CBP

Based on the surprising discovery that CBP cooperates with phosphorylation dependent activators by recruiting general transcription factors to target promoters, it was next examined whether CBP would co-fractionate with any general factors in HeLa nuclear extracts. Thus, Far-Western analyses of protein fractions were obtained after phosphocellulose chromatography. Phospho-CREB binding proteins were visualized using $^{32}$P-labeled CREB phosphorylated in vitro with PK-A ($^{32}$P-CREB). Western analysis was carried out with the same blot as described above, using affinity purified CBP antibody (CBP Ab). Far-Western ($^{32}$P-CREB) and Western (CBP-Ab) analyses of fractions were also carried out following DEAE and DE52 chromatography. Phosphocellulose, DEAE, and DE52 chromatography was performed on HeLa nuclear extracts as described by Ferreri et al., in *Proc. Natl. Acad. Sci. USA* in press (1993), which is incorporated herein by reference.

Both CBP-immunoreactive and phospho-CREB binding activities were retained on phosphocellulose columns and were eluted at 0.3–0.5M KCl. Further purification of a comparable phospho-cellulose fraction on DEAE-sepharose and DE52 resins showed that CBP was highly enriched in fractions containing TFII (E, F, H) but not TFIID activities. Although the general factor which associates directly with CBP is not known, the co-fractionation of CBP with proteins involved in basal transcription initiation suggests a testable mechanism for CBP action. In particular, the results presented herein suggest that phosphorylation-dependent activators like CREB and Jun influence assembly of late-acting factors (TFII E, F, H) during transcriptional initiation/reinitiation by interacting with CBP in a signal dependent manner.

While the invention has been described in detail with reference to certain preferred embodiments thereof, it will be understood that modifications and variations are within the spirit and scope of that which is described and claimed.

That which is claimed is:

1. A method for identifying a compound which inhibits transcription activation of cAMP and/or mitogen responsive genes, said method comprising:
 exposing cells to a test compound in the presence of a stimulant capable of activating transcription of cAMP and/or mitogen responsive genes, wherein said cells contain
  (i) a signal dependent transcription factor,
  (ii) a non-endogenous CREB-binding-protein (CBP) polypeptide that cooperates with said signal dependent transcription factor to activate transcription, wherein said polypeptide comprises at least amino acid residues 461–661 of the protein set forth in SEQ ID NO:2, and
  (iii) a reporter construct comprising DNA encoding a reporter gene, wherein said DNA is operatively linked to an inducible promoter, and wherein expression of said reporter gene is under the cooperative control of said signal dependent transcription factor and said CBP polypeptide; and thereafter
 comparing the level of expression of said reporter gene in the presence of said test compound, relative to the level of expression of said reporter gene in the absence of said test compound, wherein a reduced level of expression in the presence of said test compound indicates a compound which inhibits transcription activation of cAMP and/or mitogen responsive genes.

2. A method according to claim 1 wherein said signal dependent transcription factor is a phosphorylation dependent activator.

3. A method according to claim 1 wherein said signal dependent transcription factor is Jun, Fos, serum responsive factor, Elk or a steroid hormone receptor.

4. A method according to claim 1 wherein expression of said reporter gene is monitored by ELISA, immunoblot, immunofluorescence, or immunoprecipitation.

5. A method according to claim 1 wherein said reporter gene encodes luciferase, β-galactosidase or chloramphenicol transferase.

6. A method according to claim 5 wherein said reporter construct is CRE-lacZ, SRE-lacZ or TRE-lacZ.

7. A method according to claim 1 wherein said compound is an antibody raised against the protein binding domain of the protein set forth in SEQ ID NO:2.

8. A method according to claim 7 wherein said antibody is raised against a polypeptide fragment comprising amino acid residues 634–648 of the protein set forth in SEQ ID NO:2.

9. A method according to claim 7 wherein said antibody is raised against a polypeptide fragment comprising amino acid residues 461–661 of the protein set forth in SEQ ID NO:2.

10. A method for identifying a compound which inhibits transcription activation of cAMP and/or mitogen responsive genes in the presence of
 (i) a signal dependent transcription factor,
 (ii) a non-endogenous CREB-bindinq-protein (CBP) polypeptide comprising at least amino acid residues 461–661 of the protein set forth in SEQ ID NO:2, wherein said CBP polypeptide cooperates with said signal dependent transcription factor to activate transcription, and
 (iii) a reporter construct comprising a reporter gene operatively linked to an inducible promoter, wherein expression of said reporter gene is under the cooperative control of said signal dependent transcription factor and said CBP polypeptide; said method comprising:
 exposing the combination of (i), (ii), and (iii) to a test compound; and thereafter assaying for expression of said reporter gene, wherein a reduced level of expression in the presence of said test compound relative to the level of expression in the absence of test compound indicates a compound which inhibits transcription activation of cAMP and/or mitogen responsive genes.

11. A method according to claim 10 wherein said signal dependent transcription factor is Jun, Fos, serum responsive factor, Elk or a steroid hormone receptor.

12. A method according to claim 10 wherein expression of said reporter gene is monitored by ELISA, immunoblot, immunofluorescence or immunoprecipitation.

13. A method according to claim 10 wherein said reporter gene encodes luciferase, β-galactosidase or chloramphenicol transferase.

14. A method according to claim 13 wherein said reporter construct is CRE-lacZ, SRE-lacZ or TRE-lacZ.

15. A method for identifying a compound which promotes transcription activation of cAMP and/or mitogen responsive genes, said method comprising:

exposing cells to a test compound, wherein said cells contain
  (i) a signal dependent transcription factor,
  (ii) a non-endogenous CREB-binding-protein (CBP) polypeptide that cooperates with said signal dependent transcription factor to activate transcription, wherein said polypeptide comprises at least amino acid residues 461–661 of the protein set forth in SEQ ID NO:2, and
  (iii) a reporter construct comprising DNA encoding a reporter gene, wherein said DNA is operatively linked to an inducible promoter, and wherein expression of said reporter gene is under the cooperative control of said signal dependent transcription factor and said CBP polypeptide; and thereafter comparing the level of expression of said reporter gene in the presence of said test compound, relative to the level of expression of said reporter gene in the absence of said test compound, wherein expression indicates a compound which promotes transcription activation of cAMP and/or mitogen responsive genes.

16. A method according to claim 15 wherein expression of said reporter gene is monitored by ELISA, immunoblot, immunofluorescence, or immunoprecipitation.

17. A method for identifying a compound having transcription activating properties characteristic of a CREB binding protein, said method comprising:

exposing cells to a test compound, wherein said cells contain
  (i) a signal dependent transcription factor, and
  (ii) a reporter construct comprising DNA encoding a reporter gene, wherein said DNA is operatively linked to an inducible promoter, and wherein expression of said reporter gene is under the cooperative control of said signal dependent transcription factor and a non-endogenous CREB binding protein; and thereafter comparing the level of expression of said reporter gene in the presence of said test compound, relative to the level of expression of said reporter gene in the absence of said test compound, wherein an increased level of expression in the presence of said test compound indicates a compound having transcription activating properties characteristic of CREB binding protein.

18. A method according to claim 17 wherein expression of said reporter gene is monitored by ELISA, immunoblot, immunofluorescence or immunoprecipitation.

19. A method for identifying a substance having transcription activating properties characteristic of a signal dependent transcription factor, said method comprising:

exposing cells to a test substance, wherein said cells contain
  (i) a non-endogenous CREB-binding-protein (CBP) polypeptide that cooperates with signal dependent transcription factor to activate transcription, wherein said polypeptide comprises at least amino acid residues 461–661 of the protein set forth in SEQ ID NO:2, and
  (ii) a reporter construct comprising DNA encoding a reporter gene, wherein said DNA is operatively linked to an inducible promoter, and wherein expression of said reporter gene is under the control of said signal dependent transcription factor and said CBP polypeptide; and thereafter comparing the level of expression of said reporter gene in the presence of said test substance, relative to the level of expression of said reporter gene in the absence of said test substance, wherein an increased level of expression in the presence of said test substance indicates a substance having transcription activating properties characteristic of a signal dependent transcription factor.

20. A method according to claim 19 wherein expression of said reporter gene is monitored by ELISA, immunoblot, immunofluorescence or immunoprecipitation.

* * * * *